United States Patent
Kuzelka et al.

(10) Patent No.: US 11,318,274 B2
(45) Date of Patent: May 3, 2022

(54) SYSTEMS AND METHODS FOR A DISPOSABLE ANESTHETIC VAPORIZER

(71) Applicant: GE Precision Healthcare LLC, Milwaukee, WI (US)

(72) Inventors: Russell James Kuzelka, McFarland, WI (US); Joseph James Lacey, Cambridge, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 393 days.

(21) Appl. No.: 16/506,957

(22) Filed: Jul. 9, 2019

(65) Prior Publication Data
US 2021/0008327 A1    Jan. 14, 2021

(51) Int. Cl.
A61M 16/18    (2006.01)
A61M 16/10    (2006.01)
(Continued)

(52) U.S. Cl.
CPC ........ A61M 16/18 (2013.01); A61M 16/0057 (2013.01); A61M 16/106 (2014.02); A61M 16/183 (2013.01); A61M 16/186 (2013.01); A61M 16/0051 (2013.01); A61M 16/024 (2017.08); A61M 16/127 (2014.02); A61M 2016/1035 (2013.01); A61M 2202/0208 (2013.01); A61M 2205/121 (2013.01); A61M 2205/18 (2013.01); A61M 2205/3306 (2013.01); A61M 2205/3368 (2013.01); A61M 2205/3386 (2013.01); A61M 2205/368 (2013.01); A61M 2205/3653 (2013.01); A61M 2205/50 (2013.01); A61M 2205/502 (2013.01); A61M 2206/20 (2013.01)

(58) Field of Classification Search
CPC .. A61M 16/00; A61M 16/0087; A61M 16/01; A61M 16/022; A61M 16/08; A61M 16/0816; A61M 16/0833; A61M 16/104; A61M 16/109; A61M 16/12; A61M 16/14; A61M 16/147; A61M 16/18; A61M 16/183; A61M 16/186; A61M 2016/1035; A61M 2205/121; A61M 2205/3386
See application file for complete search history.

(56) References Cited

U.S. PATENT DOCUMENTS

| 3,556,097 A | 1/1971 | Wallace |
| 7,490,607 B2 | 2/2009 | Bottom et al. |
| (Continued) | | |

FOREIGN PATENT DOCUMENTS

WO    2016122417 A1    8/2016

Primary Examiner — Joseph D. Boecker
(74) Attorney, Agent, or Firm — McCoy Russell LLP

(57) ABSTRACT

Systems and methods are provided for delivering anesthetic agent to a patient. In one embodiment, an anesthetic vaporizer includes a housing defining a sump, the sump configured to hold a self-contained supply of liquid anesthetic agent, a heating element electrically coupled to an electrical mating component, a gas inlet passage and a gas outlet passage, a manifold fluidically coupled to the gas inlet passage and the gas outlet passage, the manifold coupled to the housing and forming a gas-tight seal with the sump, and a quick disconnect pneumatic system coupled to the gas inlet passage and the gas outlet passage, sealing the gas inlet passage and the gas outlet passage from atmosphere.

16 Claims, 8 Drawing Sheets

(51) Int. Cl.
*A61M 16/00* (2006.01)
*A61M 16/12* (2006.01)

(56) References Cited

U.S. PATENT DOCUMENTS

2009/0266358 A1\* 10/2009 Sacristan Rock ..... A61M 16/18
128/203.26
2019/0151599 A1\* 5/2019 Hanrahan ......... A61M 16/0003

\* cited by examiner

SYSTEMS AND METHODS FOR A DISPOSABLE ANESTHETIC VAPORIZER

FIELD

Embodiments of the subject matter disclosed herein relate to anesthesia systems, and more particularly, to anesthetic vaporizers.

BACKGROUND

During some medical procedures, such as surgical procedures, a patient may be placed under general anesthesia by administration of an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form. A carrier gas (e.g., a mixture of oxygen and fresh air) may flow into the vaporizer and blend (e.g., mix and converge) with the anesthetic agent vapors generated by the vaporizer. An amount of carrier gas flowing into the vaporizer may be adjusted by an operator of the vaporizer (e.g., an anesthesiologist) in order to adjust a ratio of carrier gas to anesthetic agents within the vaporizer. The mixed gases may then flow to the patient, where they may be introduced via inhalation, for example. The concentration of the anesthetic agent in the mixed gases may be controlled to ensure sufficient anesthetic agent is provided for patient comfort without compromising patient safety.

BRIEF DESCRIPTION

In one embodiment, a system for an anesthesia vaporizer cartridge includes a housing defining a sump, the sump configured to hold a self-contained supply of liquid anesthetic agent, a heating element electrically coupled to an electrical mating component, a gas inlet passage and a gas outlet passage, a manifold fluidically coupled to the gas inlet passage and the gas outlet passage, the manifold coupled to the housing and forming a gas-tight seal with the sump, and a quick disconnect pneumatic system coupled to the gas inlet passage and the gas outlet passage, sealing the gas inlet passage and the gas outlet passage from atmosphere. In this way, a simplified, self-contained anesthetic vaporizer system is provided for decreased ownership costs and increased user flexibility.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
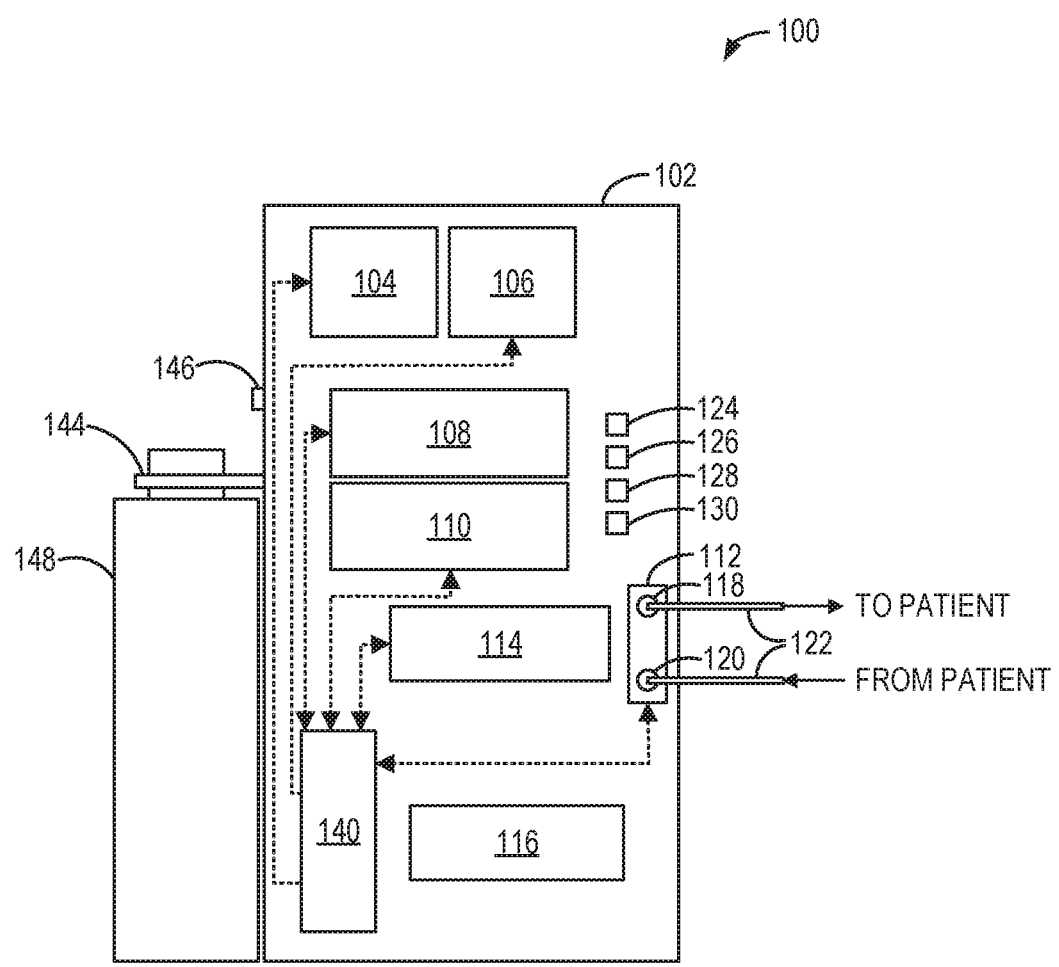
FIG. 1 schematically shows an exemplary embodiment of an anesthesia machine.

The following description relates to various embodiments of an anesthetic vaporizer system, which may be included in an anesthesia machine. Current anesthesia machines typically include anesthetic vaporizers that are manufactured by a medical supply company and designed for up to 10 years of service. Due to the long service life, the anesthetic vaporizer presents a significant cost and long term maintenance and warranty obligation to the medical equipment company. Additionally, the anesthetic vaporizer typically includes a refillable sump designed to only hold anesthetic agent from one drug manufacturer. For example, the sump may include a proprietary filler interface that prevents refilling of the sump with an anesthetic agent from a competing drug manufacturer. This obligates the medical supply company to accommodate multiple filler interface configurations, increasing anesthetic vaporizer costs, complexity, and manufacturing time due to significant verification and validation studies for each configuration. Additionally, when an operator of the anesthetic vaporizer refills the sump with a refill bottle of anesthetic agent, the operator may become exposed to the anesthetic agent due to splashing and/or leaking. Further still, some anesthetic agent may remain in the refill bottle, resulting in anesthetic agent waste that increases usage costs. Each refill bottle may have a relatively low volume capacity (e.g., 250 mL), and so a large number of refill bottles may be stored at a point of use (e.g., a healthcare facility) and used in a single day, further increasing an amount of waste associated with anesthetic agent refilling.

Thus, according to embodiments disclosed herein, a simplified anesthetic vaporizer system is provided. The embodiments disclosed herein may include a single or limited use self-contained anesthetic vaporizer cartridge that may be installed in an anesthesia machine via a universal connection. Further, the embodiments disclosed herein may include different vaporizer engines that are integrated with a sump for decreased complexity. The different vaporizer engines may each include localized heating for providing latent heat of vaporization. The embodiments disclosed herein may further include increased anesthetic agent volume capacities, reducing a need to replenish the supply of anesthetic agent between procedures and reducing anesthetic agent waste. Additionally, the embodiments disclosed herein may include a pre-filled sump that is only refillable by the drug manufacturer.

The embodiments disclosed herein may provide several advantages. For example, the embodiments disclosed herein provide an anesthetic vaporizer system that is cheaper to manufacture and maintain, resulting in lower ownership costs. For example, due to the reduced service life, long service life reliability testing and warranty obligations are reduced, decreasing manufacturing costs. Additionally, manufacturing costs may be decreased due to decreased system complexity, such as due to the integration of the sump and the vaporizer engine. The universal connection enables the operator to seamlessly interchange different anesthetic agent cartridges, such as containing different anesthetic agents, different anesthetic agent volumes, or anesthetic agent manufactured by different companies, for increased flexibility. Further, because the sump comes pre-filled and may not be refilled by the operator, operator exposure to anesthetic agent is reduced. This may also reduce refilling-associated anesthetic agent waste, further reducing ownership costs. Further, the embodiments disclosed herein may provide a quick response time compared with bulk boiling due to the localized heating, which also enables high concentrations of anesthetic agent at high flow rates may be maintained.

Figure 2A:
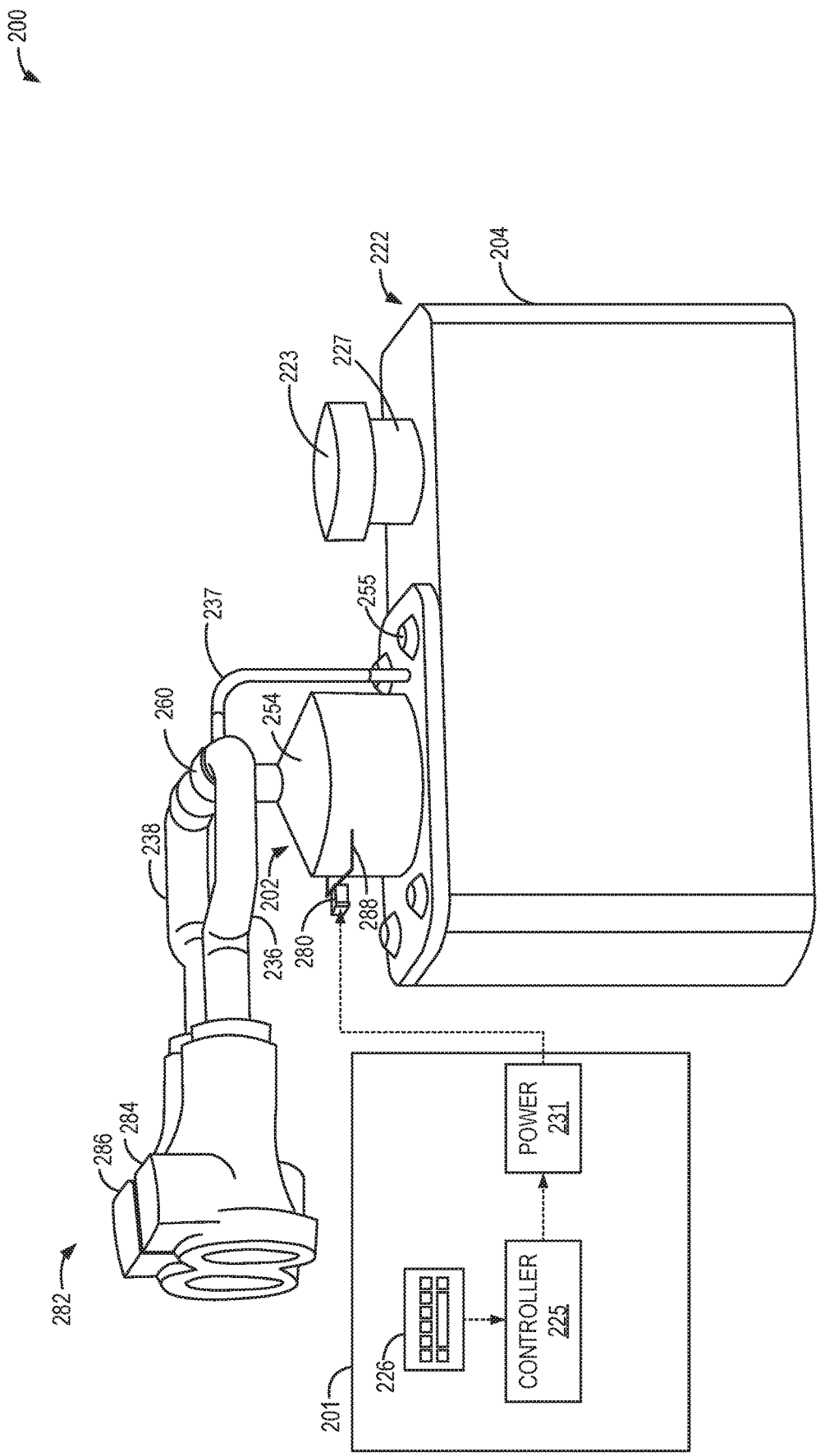
FIG. 2A shows a perspective view of a first exemplary embodiment of an anesthetic vaporizer cartridge.
Figure 2B:
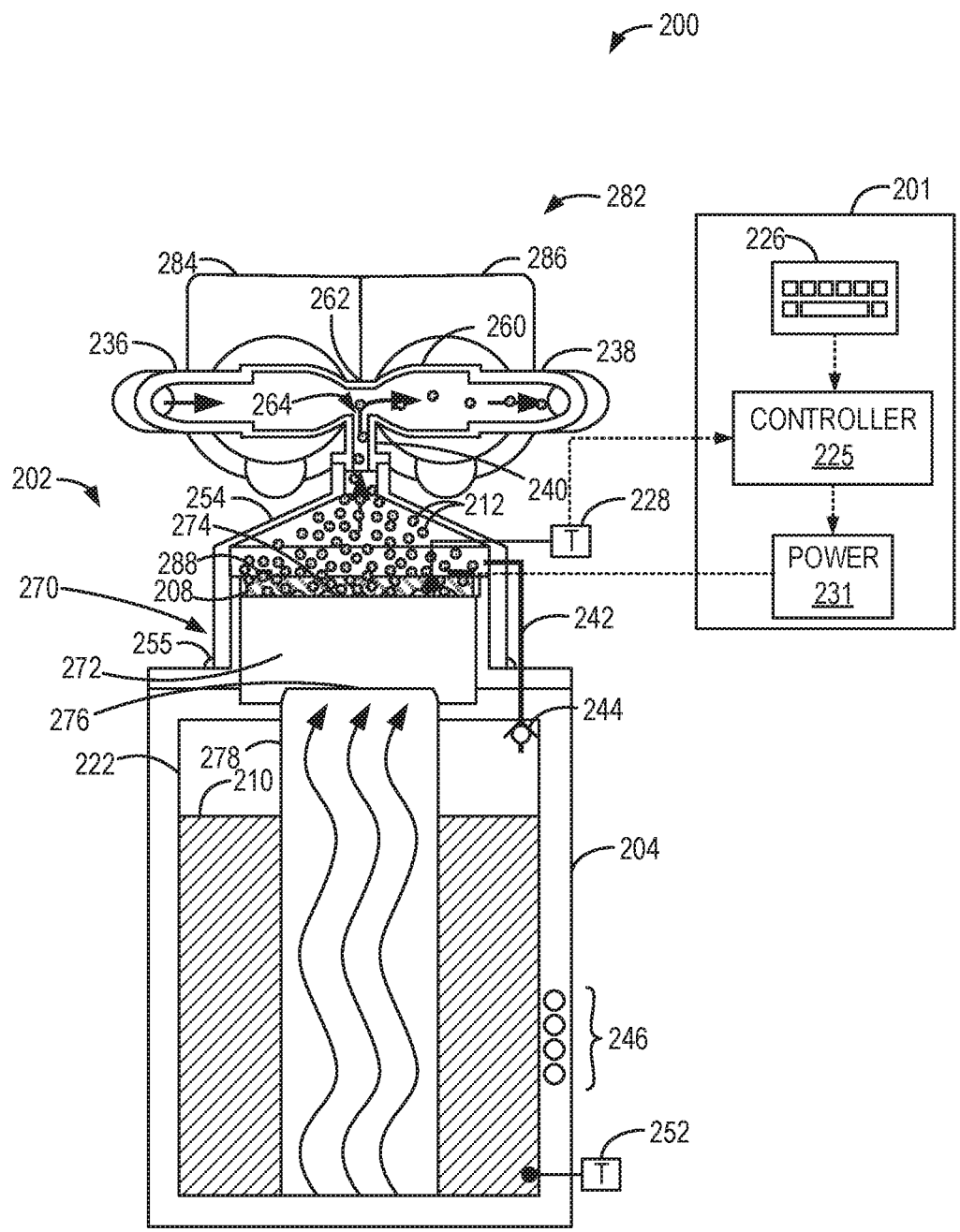
FIG. 2B shows a cross-sectional view of the first exemplary embodiment of the anesthetic vaporizer cartridge.
Figure 3:
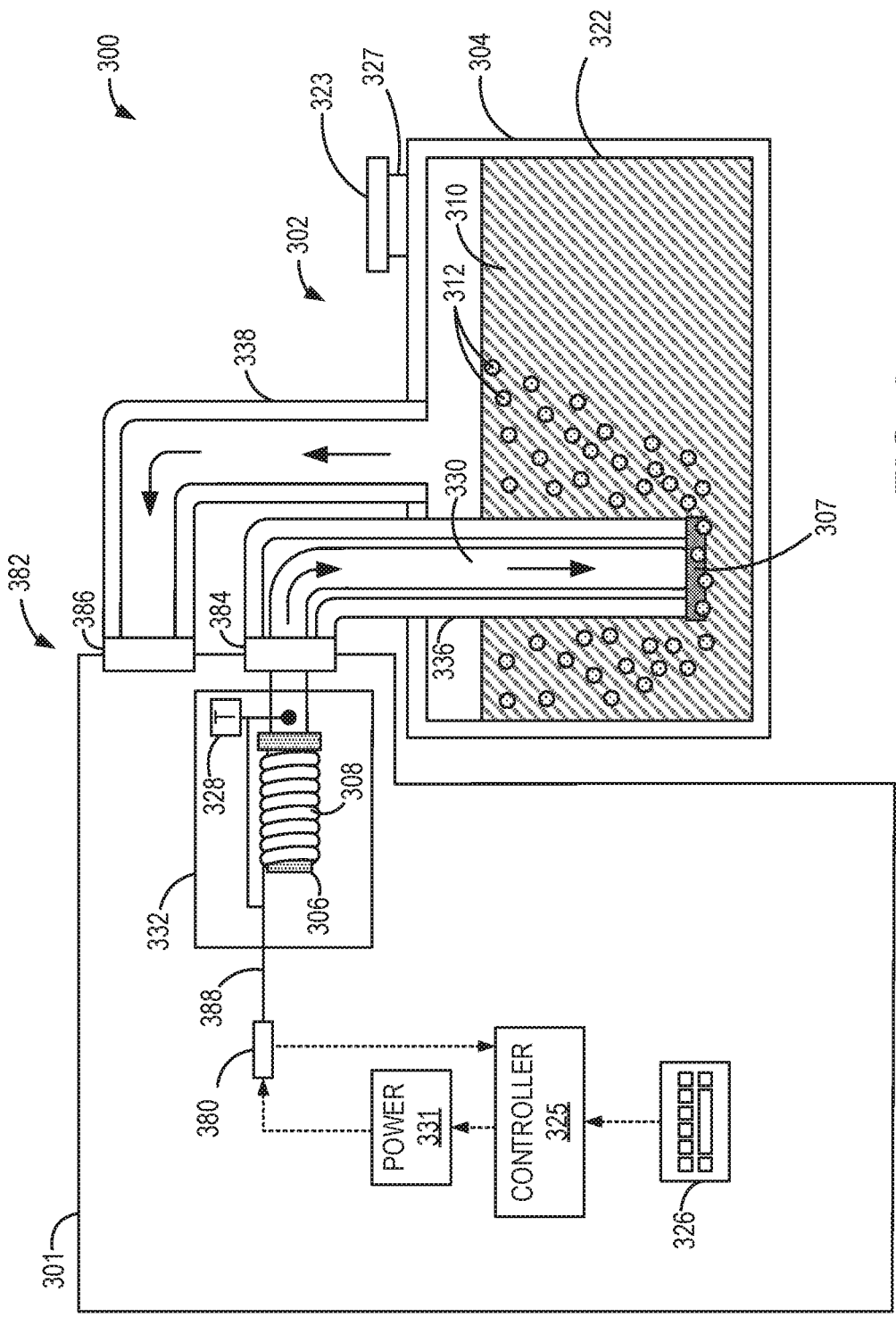
FIG. 3 schematically shows a second exemplary embodiment of an anesthetic vaporizer cartridge.
Figure 4:
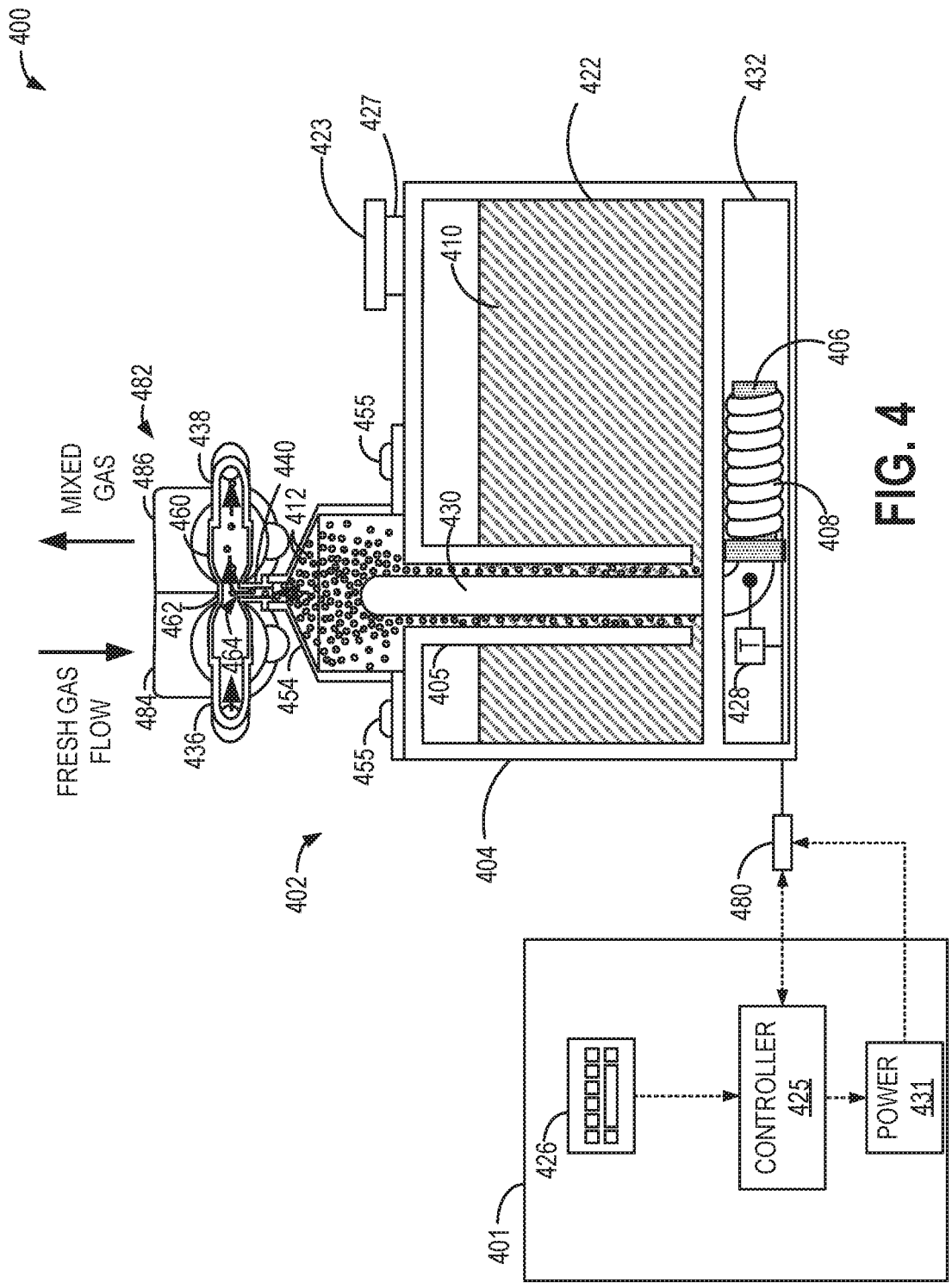
FIG. 4 schematically shows a third exemplary embodiment of an anesthetic vaporizer cartridge.

FIG. 1 schematically shows an exemplary embodiment of an anesthesia machine. FIGS. 2A and 2B show a first embodiment of an anesthetic vaporizer cartridge, which may be included in the anesthesia machine of FIG. 1. FIG. 3 shows a second embodiment of an anesthetic vaporizer cartridge, which may be included in the anesthesia machine of FIG. 1. FIG. 4 shows a third embodiment of an anesthetic vaporizer cartridge, which may be included in the anesthesia machine of FIG. 1. A controller may track a volume of liquid anesthetic agent remaining in the anesthetic vaporizer cartridge between and during use, such as using the exemplary fill level sensing system shown in FIG. 5, and alert an operator to replace the cartridge when the volume is low, such as according to the example method of FIG. 6. The amount of vaporized anesthetic agent produced by the anesthetic agent system may be controlled by adjusting an amount of power supplied to a heating element according to the example method of FIG. 7.

FIG. 1 schematically shows an example anesthesia machine 100. Anesthesia machine 100 includes a frame (or housing) 102. In some embodiments, frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

Anesthesia machine 100 also includes an anesthesia display device 104, a patient monitoring display device 106, a respiratory gas module 108, one or more patient monitoring modules, such as a patient monitoring module 110, a ventilator 112 (explained in more detail below), an anesthetic vaporizer 114, and an anesthetic agent storage bay 116. Anesthesia machine 100 may further include a main power indicator 124, a system activation switch 126 (which, in one example, permits gas flow when activated), an oxygen flush button 128, and an oxygen control 130.

In some embodiments, anesthetic vaporizer 114 may be removably coupled to anesthesia machine 100. For example, anesthetic vaporizer 114 may be an insertable, cartridge-style anesthetic vaporizer that may be easily removed from anesthesia machine 100 (e.g., without disassembly of anesthesia machine and/or without tools) and replaced, such as when a store of anesthetic agent within anesthetic vaporizer 114 is depleted or when different vaporizer characteristics are desired (such as a different anesthetic agent, a different volume capacity, etc.). Example embodiments of anesthetic vaporizer 114 will be described below with respect to FIGS. 2A-2B, 3, and 4. Anesthetic vaporizer 114 may vaporize the anesthetic agent and combine the vaporized anesthetic agent with one or more medical grade gases (e.g., oxygen, air, nitrous oxide, or combinations thereof), which may then be delivered to a patient.

Anesthesia machine 100 may additionally include an integrated suction, an auxiliary oxygen flow control, and various other components for providing and/or controlling a flow of the one or more medical grade gases to the patient. For example, anesthesia machine 100 includes one or more pipeline connections 146 to facilitate coupling of the anesthesia machine to pipeline gas sources. Additionally, anesthesia machine 100 includes a cylinder yoke 144, which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via the ventilator 112. The anesthesia machine may also include a serial port, a collection bottle connection, a cylinder wrench storage area, and an anesthesia gas scavenging system.

The ventilator 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ventilator 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via the expiratory port 120, where carbon dioxide may be removed from the expiratory gases via the absorber canister.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be controlled by the operator via one or more flow adjustment devices. For example, the flow adjustment devices may include analog and/or digital adjustment dials and/or other user input devices configured to actuate one or more flow control valves of anesthesia machine 100. In some embodiments, a first flow control valve may be positioned between the gas source(s) and the anesthetic vaporizer 114 and may be actuatable via the flow adjustment devices to a fully opened position, a fully closed position, and a plurality of positions between the fully opened position and the fully closed position.

Anesthesia machine 100 may additionally include one or more valves configured to bypass gases from the gas source(s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via the inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further still, the respiratory gas module 108 may measure respiration rate, minimum alveolar concentration, patient oxygen concentration, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ventilator 112 may optionally be coupled to a breathing circuit (not shown) including a plurality of tubes (e.g., gas passages) 122. The breathing circuit may be coupled between an airway of a patient (e.g., via a breathing mask positioned to enclose the mouth and/or nose of the patient or a tracheal intubation tube) and the inspiratory port 118. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patient (e.g., through inhalation) via the inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 114, the ventilator 112, the respiratory gas module 108, the anesthesia display device 104, and the patient monitoring display device 106.

The controller receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled via an input device (e.g., keyboard, touchscreen, etc.) coupled to the electronic controller of the anesthesia machine 100. The controller 140 may display operating parameters of the anesthesia machine 100 via the anesthesia display device 104 and/or the patient monitoring display device 106. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

Controller 140 is shown in FIG. 1 for illustrative purposes, and it is to be understood that controller 140 may be located in various locations within, around, and/or remote from anesthesia machine 100. As an example, controller 140 may include multiple devices/modules that may be distributed throughout anesthesia machine 100. As such, controller 140 may include a plurality of controllers at various locations within anesthesia machine 100. As another example, additionally or alternatively, controller 140 may include one or more devices/modules that are external to anesthesia machine 100, located proximate to (e.g., in a same room) or remote from (e.g., a remote server) anesthesia machine 100. In each example, the multiple devices/modules may be communicatively coupled through wired and/or wireless connections.

Traditionally, an anesthetic vaporizer includes a sump that supplies a liquid anesthetic agent to a separate vaporizing chamber, which may employ various vaporizer engines (e.g., liquid to gas conversion components) to vaporize the liquid anesthetic agent for delivery to a patient. As the anesthesia machine is used, the volume of liquid anesthetic agent in the sump decreases, and so the sump may be periodically refilled in order to maintain the supply of anesthetic agent to the vaporizing chamber during use. Refilling the sump may result in anesthetic agent waste due to spray-back, leakage, and spills, which may also expose an operator to the anesthetic agent. Additionally, the anesthetic vaporizer may further include conduits, valves (e.g., check valves and shut-off valves), and a pump to supply the liquid anesthetic to the vaporizing chamber from the sump. Such components may be costly and present additional sources of degradation that may result in high service costs for repair or replacement. The anesthetic vaporizer may be manufactured to have at least a 10 year service life, further increasing anesthetic vaporizer costs. Further still, the anesthetic vaporizer may have low portability due to the components and their weight.

Therefore, FIGS. 2A and 2B show a first exemplary embodiment of an anesthetic vaporizer cartridge 200 that may be installed in an anesthesia machine 201 (which may represent anesthesia machine 100 shown in FIG. 1, for example). As one example, anesthetic vaporizer cartridge 200 may be anesthetic vaporizer 114 of FIG. 1. In particular, anesthetic vaporizer cartridge 200 is a self-contained disposable (or reusable) anesthetic vaporizer system having a capillary wick-based vaporizer engine. FIG. 2A shows a perspective view of anesthetic vaporizer cartridge 200, highlighting external surfaces of anesthetic vaporizer cartridge 200, whereas FIG. 2B shows a cross-sectional view highlighting internal components of anesthetic vaporizer cartridge 200. FIGS. 2A and 2B will be described collectively.

Anesthetic vaporizer cartridge 200 includes a housing 204 that defines a sump 222. As shown in FIG. 2B, sump 222 stores a liquid anesthetic agent 210 therein. The liquid anesthetic agent 210 may be isoflurane, sevoflurane, or another liquid anesthetic agent of similar volatility, for example. In one embodiment, particularly where anesthetic vaporizer cartridge 200 is designed for single-use applications, housing 204 is comprised of one or more plastics (e.g., polycarbonate, polypropylene, polyurethane) in order to reduce anesthetic vaporizer weight and cost. Such an embodiment may increase portability for usage in rural or field settings, for example, or any other setting outside of a traditional health care facility. In other embodiments, housing 204 may be at least partially comprised of metal.

As shown in FIG. 2A, sump 222 includes a fill port (or neck) 227 that is sealed by a cap 223. Anesthetic vaporizer cartridge 200 may be delivered to a point of use (e.g., a healthcare facility or other location) pre-filled with liquid anesthetic agent 210 in sump 222, and thus, sump 222 may be sealed by cap 223 by an agent manufacturer (e.g., at a factory). In one embodiment, cap 223 may include a mechanism that prevents removal of the cap outside of the factory so that sump 222 may only be filled/refilled by the agent manufacturer. As an example, anesthetic vaporizer cartridge 200 may be manufactured at low cost, enabling disposal at the point of use for single use implementation. Alternatively, anesthetic vaporizer cartridge 200 may be returned to the manufacturer for a limited number of factory refills of liquid anesthetic agent 210, after which anesthetic vaporizer cartridge 200 may be disposed of or rebuilt. The number of fills may be tracked at the factory or at the point of use (e.g., based on a serial number of anesthetic vaporizer cartridge 200) via an electronic or physical counter, for example.

Sump 222 may be provided in a variety of volume capacities and with different liquid anesthetic agents stored therein, tailoring anesthetic vaporizer cartridge 200 to different medical procedures and uses. As one example, an operator of the anesthesia machine may select the particular anesthetic vaporizer cartridge 200 to use from a plurality of options based on the anesthetic agent to be delivered and a length the procedure to be performed. For example, each of the plurality of options may include a different type of liquid anesthetic agent and/or a different volume of liquid anesthetic agent contained within the sump (e.g., due to different sump capacities). The operator may select larger sump capacities for longer procedures (or procedures using high anesthetic agent flow rates) and smaller sump capacities for shorter procedures (or procedures using low anesthetic agent flow rates). Further, in some embodiments, sump 222 may have a large enough capacity to perform multiple procedures without the anesthetic vaporizer cartridge 200 having to be replaced (e.g., due to low liquid anesthetic agent 210 volume). Thus, sump 222 holds a self-contained supply of liquid anesthetic agent 210 that may not be replenished at the point of use.

Anesthetic vaporizer cartridge 200 may be a removable unit that is fluidically connected to and disconnected from gas passages of anesthesia machine 201 via a quick disconnect pneumatic system 282, which includes an input 284 and an output 286. Quick disconnect pneumatic system 282 pneumatically seals anesthetic vaporizer cartridge 200 from atmosphere so that when anesthetic vaporizer cartridge 200 is disconnected from the anesthesia machine 201 (e.g., quick disconnect pneumatic system 282 is not connected to a corresponding feature on the anesthesia machine), anesthetic vaporizer cartridge 200 is gas-tight and liquid-tight (e.g., completely sealed) stand-alone unit. Input 284 is configured to connect to a fresh gas flow of anesthesia machine 201 and, when connected, enables fresh gas (e.g., oxygen, air, nitrous oxide, and combinations thereof) to flow from anesthesia machine 201 to anesthetic vaporizer cartridge 200 via a gas inlet passage 236. The fresh gas flow may be provided via one or more gas pipelines (e.g., via pipeline connections 116 shown in FIG. 1) and/or one or more gas-holding cylinders (e.g., via cylinder yoke 144 of FIG. 1). Output 286 is configured to connect to a mixed gas flow of anesthesia machine 201 and, when connected, enables mixed gas (containing both fresh gas and anesthetic agent vapor 212) to flow from anesthetic vaporizer cartridge 200 to the anesthesia machine via a manifold 254 and a gas outlet passage 238, as will be elaborated below. Further, in some embodiments, a pressure equalization tube 237 (shown in FIG. 2A) may directly fluidically couple sump 222 to gas inlet passage 236 to allow pressure communication between gas inlet passage 236 and sump 222. For example, pressure equalization tube 237 may be included when liquid anesthetic agent 210 has a sub-ambient vapor pressure. In other embodiments, such as when liquid anesthetic agent 210 has a vapor pressure above ambient pressure, pressure equalization tube 237 may be omitted.

Prior to use, anesthetic vaporizer cartridge 200 may be installed in anesthesia machine 201 by fluidically coupling the anesthesia machine gas flow to anesthetic vaporizer cartridge 200 via quick disconnect pneumatic system 282 and electrically coupling a heating element 208 of anesthetic vaporizer cartridge 200 to a power source 231 via an electrical connector 280. Quick disconnect pneumatic system 282 may be a simple, universal connection that enables anesthetic vaporizer cartridges from any drug manufacturer to be installed in the same anesthesia machine. Then, after use (or when sump 222 no longer holds enough liquid anesthetic agent 210 for completing a procedure), anesthetic vaporizer cartridge 200 may be disconnected from the anesthesia machine gas flow via quick disconnect pneumatic system 282 and disconnected from power source 231 via electrical connector 280. Anesthetic vaporizer cartridge 200 may then be returned to the manufacturer for refilling or refurbishing, and a different anesthetic vaporizer (holding the same or different liquid anesthetic agent at a same or different volume, depending on the next procedure to be performed) may be installed in anesthesia machine 201.

In one embodiment, anesthetic vaporizer cartridge 200 may be electrically coupled to a controller 225 via electrical connector 280. In another embodiment, controller 225 may be electrically coupled to power source 231, which is electrically coupled to heating element 208 of anesthetic vaporizer cartridge 200, without being directly electrically coupled to heating element 208 or any other component of anesthetic vaporizer cartridge 200. Controller 225 may be a dedicated controller of anesthetic vaporizer cartridge 200 or may be a controller of anesthesia machine 201 (e.g., controller 140 shown in FIG. 1). Thus, controller 225 may not be included in the disposable anesthetic agent cartridge of anesthetic vaporizer cartridge 200. Similarly, power source 231 may be included in anesthesia machine 201, as shown, or as an otherwise non-disposable electronic portion of the anesthetic vaporizer cartridge. Thus, controller 225 and/or power source 231 may be temporarily connected to each disposable anesthetic vaporizer cartridge as it is used without the controller and the power source being replaced when the operator switches between cartridges. In other embodiments, power source 231 may be a disposable or rechargeable battery mounted on the exterior of anesthetic vaporizer cartridge 200 that includes a direct, permanent electrical connection with heating element 208, making power source 231 an integral component of the disposable unit. In some such embodiments, electrical connector 280 may temporarily connect power source 231 to controller 225, such as when electronic control of heating element 208 is utilized.

Electrical connector 280 may be a quick-disconnect mating component that, when mated with a complimentary mating component of power source 231 and/or controller 225, provides a temporary connection to power source 231 and/or controller 225. As shown in FIGS. 2A and 2B, a terminal of electrical connector 280 may be positioned external to manifold 254, on an exterior of anesthetic vaporizer cartridge 200, while wires 288 extend from the terminal through a housing of manifold 254 and to the interior of manifold 254, where they form a permanent electrical connection with heating element 208.

Figure 5:
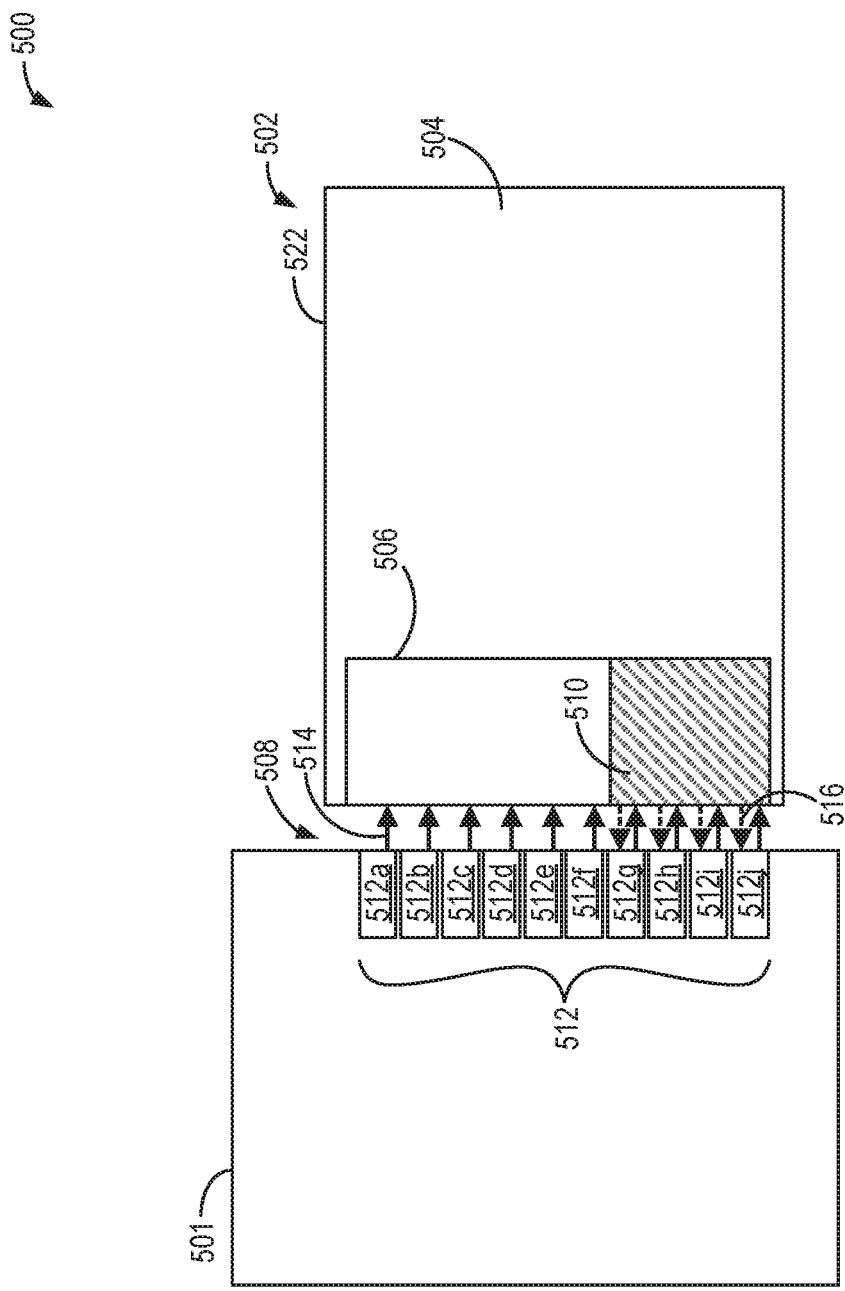
FIG. 5 schematically shows an exemplary embodiment of an interface between an anesthesia machine and an anesthetic vaporizer cartridge for determining a remaining volume of anesthetic agent in the anesthetic vaporizer cartridge.
Figure 6:
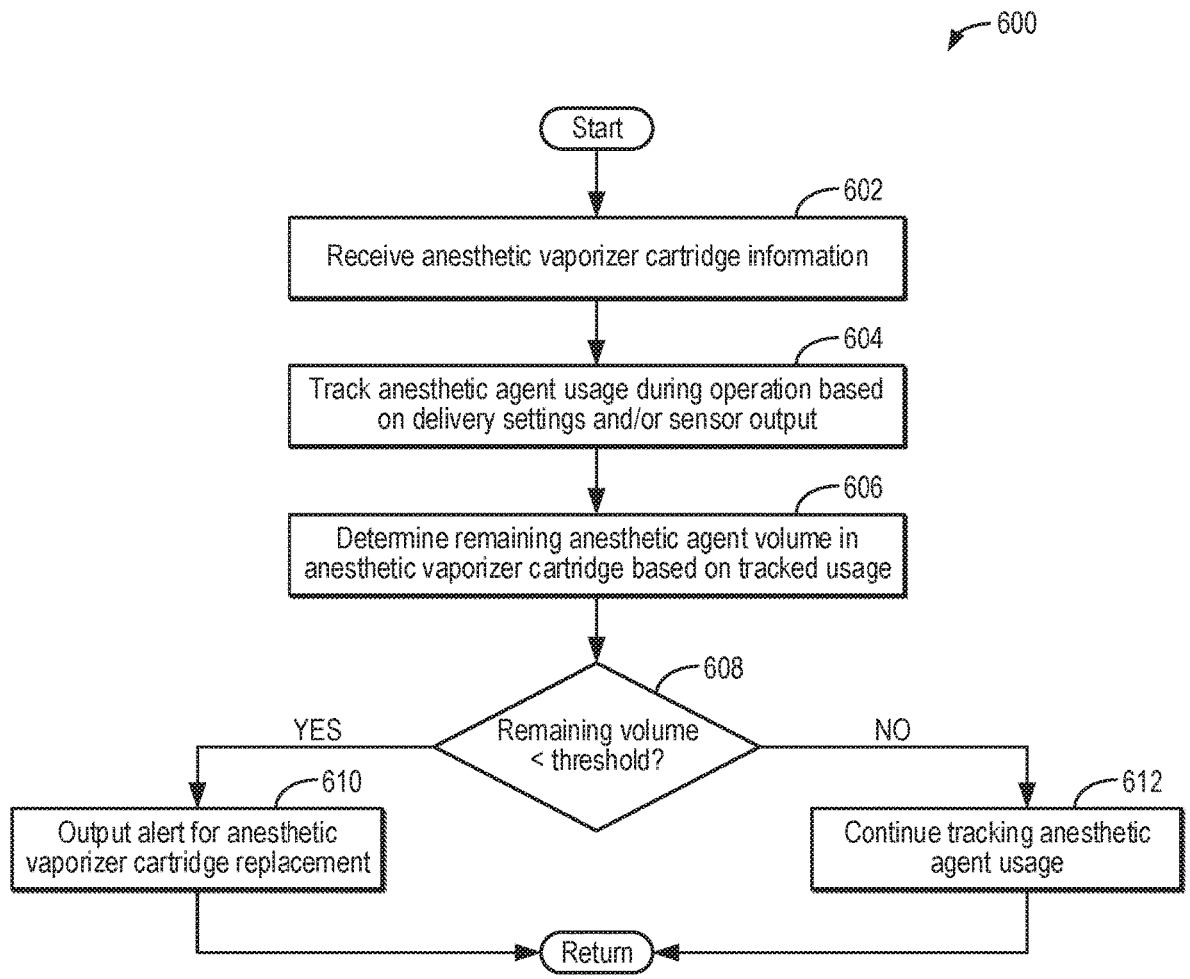
FIG. 6 is a flow chart illustrating an exemplary embodiment of a method for prompting replacement of an anesthetic vaporizer cartridge installed in an anesthesia machine.

Controller 225 may track anesthetic agent usage in order to determine when anesthetic vaporizer cartridge 200 is nearing empty and needs to be replaced, as will be elaborated with respect to FIGS. 5 and 6. Because the volume capacity of sump 222 may be known, in one embodiment, the controller may estimate the amount of anesthetic agent remaining in the sump without additional output from a level sensor, reducing anesthetic vapor cartridge 200 components and cost. For example, controller 225 may output an alert to the operator so that the operator is prompted to remove the current, empty anesthetic vaporizer cartridge from anesthesia machine 201 and install a new, full anesthetic vaporizer cartridge in anesthesia machine 201.

In one embodiment, anesthetic vaporizer cartridge 200 may include non-volatile memory (e.g., EEPROM, a microcontroller, etc.), whereby anesthesia machine 201 (e.g., controller 225) may query the cartridge for its fill level upon insertion. As an example, the integral non-volatile may contain programmed information including last known fill level, drug identification, lot/date code, etc. The integral non-volatile memory may communicate with the host anesthesia system (e.g., controller 225) through a power limited supply (+5VDC and/or +3.3VDC) and communications bus interface (e.g., I2C/SPI/CAN) via a pogo-pin, spring contact, or similar connection. For example, FIG. 2B shows contact pads 246 positioned on housing 204. Contact pads 246 may include a power input, a clock line (e.g., SCL), a data line (e.g., SDA), and a ground for signal and power connections to controller 225, for example. Further, during anesthetic delivery, the anesthesia machine (e.g., controller 225) may calculate and track anesthetic agent consumption to update the fill level stored in the non-volatile memory of anesthetic agent cartridge 200 upon delivery completion, as will be elaborated below with respect to FIG. 6.

However, in other embodiments, a level sensor may be included in anesthetic vaporizer cartridge 200 and/or the anesthesia machine for providing an electronic feedback signal to controller 225 regarding the volume (or level) of liquid anesthetic agent 210 remaining in sump 222. In one non-limiting example, multiple discrete reflective optical sensors on the mating anesthesia machine may monitor discrete liquid anesthetic agent levels within the anesthetic agent cartridge through an optical window on the anesthetic agent cartridge, as will be further described below with respect to FIG. 5. As other non-limiting examples, a capacitive, optical time of flight, or inductive level sensor may be included within anesthetic agent cartridge 200 for monitoring the level of liquid anesthetic agent contained therein and may output a corresponding signal to controller 225.

As shown in FIG. 2B, anesthetic vaporizer cartridge 200 further includes a capillary pump 270, which is partially disposed within sump 222. Capillary pump 270 includes a vaporization zone 272, which includes a vapor release area 274 and a liquid intake area 276, and a wick 278 that is at least partially submerged in the liquid anesthetic agent 210 in sump 222. As shown, wick 278 may extend to a bottom of sump 222 and touch (e.g., make contact with) an interior surface of housing 204. In other embodiments, there may be a space between the interior surface of housing 204 and wick 278 such that wick 278 does not contact the interior surface of housing 204. Capillary pump 270 may be comprised of metal and/or ceramic. Wick 278 may be comprised of a single material or a stacked wick comprised of more than one material (such as ceramic and metal and/or a plurality of metals). Vaporization zone 272 may be comprised of a material that resists distortion or damage from heat. For example, in the embodiment shown in FIG. 2B, vaporization zone 272 is in direct contact with a heating element 208 (e.g., at the vapor release area 274) that is housed within manifold 254, forming a vaporizing chamber 202. Thus, capillary pump 270 extends between manifold 254 and sump 222, and vaporizing chamber 202 is integrated with sump 222 (e.g., as a single unit). Manifold 254 may be attached to sump 222 via a plurality of fasteners 255 (which may be screws or bolts, for example), making manifold 254 removable from sump 222 while forming a gas-tight seal with sump 222 while attached.

During operation, vaporization zone 272 is heated via heating element 208 in order to provide energy for the phase change of liquid anesthetic agent 210 to anesthetic agent vapor 212, known as latent heat of vaporization, at vaporization zone 272. The heat supplied by heating element 208 also results in a temperature gradient between vaporization zone 272 and a bottom of wick 278. In the embodiment shown in FIGS. 2A and 2B, heating element 208 is a conductive heater that converts electrical energy into thermal energy (e.g., heat) and transfers that thermal energy to vaporization zone 272 via thermal conduction. However, in other embodiments, heating element 208 may be an inductive heater. Heating element 208 may receive electrical power from power source 231 via electrical connector 280 and wires 288 in response to a command signal from controller 225, as will be further described below. Because heating is localized to vaporization zone 272, anesthetic agent vapor 212 may be rapidly available upon activating heating element 208 and less power may be used to produce the anesthetic agent vapor 212 versus bulk boiling anesthetic agent 210 in sump 222.

Due to the temperature gradient and capillary force, liquid anesthetic agent 210 is drawn through capillary pump 270 via capillary forces from a lower temperature area (e.g., the bottom of wick 278) to a higher temperature area (e.g., vaporization zone 272). That is, liquid anesthetic agent 210 is drawn up wick 278 and enters vaporization zone 272 via liquid intake area 276. The liquid anesthetic agent 210 is heated and converted to anesthetic agent vapor 212 in vaporization zone 272, and the anesthetic agent vapor 212 is released from vaporization zone 272 (and the capillary pump 270) at vapor release area 274. Heat travels opposite the fluid flow, from vaporization zone 272 toward wick 278, as a cooling flow of fresh liquid anesthetic agent 210 travels toward vaporization zone 272, resulting in a dynamic balance of heat flux, liquid flow, and evolved vapor.

In one embodiment, controller 225 may adjust the amount of heat generated at vaporization zone 272 (e.g., via heating element 208) to control an amount of anesthetic agent vapor 212 generated, as will be elaborated below with respect to FIG. 7. As an example, when a desired anesthetic agent flow rate (or concentration) to deliver to a patient is low, an amount of power provided to heating element 208 may be lower, and when the desired anesthetic agent flow rate (or concentration) is high, the amount of power provided to heating element 208 may be higher. The controller may receive the desired anesthetic agent flow rate (or concentration) from an operator via a human-machine interface (HMI) 226 operationally coupled to controller 225 (e.g., via wired or wireless communication) and configured to transmit an input signal to controller 225, at least in one embodiment. HMI 226 may include one or more of a mouse, a keyboard, a voice input device, a touch input device for receiving a gesture from the operator, an optical camera or other motion input device for detecting non-touch gestures and other motions by the operator, and other comparable input devices, as well as associated processing elements capable of receiving user input from the operator. Additionally, HMI 226 may include one or more of a display for providing visual alerts or text-based messages and a speaker for providing audible alerts or messages to the operator. Thus, HMI 226 may include both a user input device and an output device.

In some embodiments, a temperature sensor may be coupled to vaporization zone 272 or heating element 208 to provide temperature feedback to controller 225 for controlling the amount of power provided to heating element 208 from power source 231 (and thus the amount of anesthetic agent vapor 212 produced). For example, FIG. 2B shows a first temperature sensor 228 coupled to heating element 208 for measuring a temperature of heating element 208. For example, a probe portion of first temperature sensor 228 may be positioned in the interior of manifold 254 and in direct contact with heating element 208, while an electronic portion may be located exterior to manifold 254. Some embodiments may further include a second temperature sensor 252 for measuring a temperature of liquid anesthetic agent 210 within sump 222. For example, a probe portion of second temperature sensor 252 may be positioned within sump 222, at or near a bottom of sump 222, and configured to be submerged within the liquid anesthetic agent 210, which an electronic portion may be located on the exterior of housing 204. However, in other embodiments, the amount of power provided to heating element 208 may be controlled without temperature feedback. In still another embodiment, anesthetic vaporizer cartridge 200 may be manually controlled by the operator (e.g., via a dial) instead of being electronically controlled by controller 225. For example, a pre-set amount of power may be provided to heating element 208 from power source 231 based on the dial position.

Further, the composition and structure of the materials comprising capillary pump 270, including pore size, pore size distribution, degree of porosity, and thermal conductivity, affect the resulting liquid permeability and capillary pressure. For example, materials having higher liquid permeability generally provide higher volume throughput, and materials with higher capillary pressure generally provide higher pressure vapor output. Thus, capillary pump 270 may be tailored for a specific application, such as for a particular anesthetic agent, for an anesthetic agent flow rate (or concentration) range, for a specific medical procedure, etc., to achieve desired pressure and flow effects. In this way, the amount of anesthetic agent vapor 212 generated by anesthetic vaporizer cartridge 200 may be precisely and simply controlled by both the selected capillary pump 270 composition and structure and the amount of power provided to heating element 208.

Additionally, vaporization zone 272 and manifold 254 may be designed to withstand relatively high vapor pressures, such as up to approximately 2270 mmHg (or 44 psi) at approximately 50° C. Therefore, in some embodiments, anesthetic vaporizer cartridge 200 may include one or more pneumatic couplings to pneumatically couple pressure generated in manifold 254 (e.g., due to anesthetic agent vapor 212 generation at vaporization zone 272) to sump 222. The embodiment shown in FIG. 2B includes a pneumatic coupling 242 and a check valve 244 coupled to pneumatic coupling 242, although other embodiments may include more than one pneumatic coupling, each including a check valve coupled thereto. Pneumatic coupling 242 extends from the interior of manifold 254, at a position above vaporization zone 272 and heating element 208, to the interior of sump 222 through a top of housing 204. Pneumatic coupling 242 may form a gas-tight passage between manifold 254 and sump 222. Check valve 244 may enable vapor (e.g., vaporized anesthetic agent) to flow from manifold 254 to sump 222, such as to a vapor space above the fill level of liquid anesthetic agent 210. Coupling the generated vapor pressure into the sump 222 via the check valve 244 may assist capillary pump 270 in keeping vaporization zone 272 supplied with liquid anesthetic agent 210 during high flow and high concentration cases, for example.

As mentioned above, other embodiments may include an inductive heater. In some such embodiments, wick 278 may be a meshed metal wick. Alternatively, capillary pump 270 may further include a meshed metal sleeve positioned around wick 278 and positioned within sump 222. The meshed metal wick or meshed metal sleeve may be comprised of a ferromagnetic material for inductive heating by the inductive heater, which may be positioned external to the sump, for example, and the inductive heating may generate the anesthetic agent vapor 212. In such embodiments, the larger the surface area and the thinner the metal mesh, the more responsive the heat transfer to the liquid anesthetic agent 210 may be, resulting in increased heating efficiency and reduced power consumption, for example.

The evolved anesthetic agent vapor 212 (e.g., vaporized anesthetic agent) may exit vaporizing chamber 202 via a vapor delivery passage 240 coupled to manifold 254 and flow to a venturi 260. An inlet of venturi 260 is coupled to gas inlet passage 236, through which fresh gas flow is provided to venturi 260, and an outlet of venturi 260 is coupled to gas outlet passage 238. Venturi 260 includes a tapered tube 262. As shown in FIG. 2B, a diameter of tapered tube 262 gradually decreases from the inlet of venturi 260 until a minimum diameter is reached. The minimum diameter may be maintained throughout a throat region 264 before gradually increasing again toward the outlet of venturi 260. The diameter of the inlet of venturi 260 may be the same as the diameter the outlet of venturi 260, as shown. Vapor delivery passage 240, which has a smaller diameter than each of gas inlet passage 236 and gas outlet passage 238, is shown coupled to tapered tube 262 of venturi 260 at throat region 264. As the fresh gas flows through tapered tube 262, a pressure drop occurs at throat region 264 that pulls the anesthetic agent vapor 212 into the fresh gas stream, resulting in mixed gas containing both the fresh gas from the fresh gas flow and the anesthetic agent vapor 212. For example, the mixed gas may be a homogenous mixture of the fresh gas and the anesthetic agent vapor 212. The mixed gas may then be delivered to the patient via an inspiratory limb of a breathing circuit of anesthesia machine 201 (e.g., via inspiratory port 118 described with respect to FIG. 1).

By providing anesthetic vaporizer cartridge 200 as a single-use cartridge that may be refilled at the anesthetic agent manufacturer instead of refilled at the point of use, operator/clinician exposure to anesthetic agent is reduced by eliminating splashing/leaking of the anesthetic agent during refill. Additionally, usage costs and environmental pollution may be reduced by reducing anesthetic agent waste associated with refilling a vaporizer sump on-site via a refill bottle. Further still, the single-use cartridge may enable easier and more cost effective anesthetic agent delivery in rural areas, outside of a large healthcare facility setting.

Turning now to FIG. 3, a second exemplary embodiment of an anesthetic vaporizer cartridge 300 is shown, which may be installed in an anesthesia machine 301 (which may correspond to anesthesia machine 100 shown in FIG. 1, for example). Anesthetic vaporizer cartridge 300 may be similar to anesthetic vaporizer cartridge 200 of FIGS. 2A and 2B in that anesthetic vaporizer cartridge 300 is a self-contained disposable (or reusable) anesthetic vaporizer system, but unlike anesthetic vaporizer cartridge 200, anesthetic vaporizer cartridge 300 employs a bubble-through architecture.

Anesthetic vaporizer cartridge 300 includes a housing 304 that defines a sump 322. Housing 304 may be comprised of the same materials as housing 204 of FIGS. 2A-2B, for example. Sump 322 stores a liquid anesthetic agent 310 therein, which may be similar to liquid anesthetic agent 210 of FIGS. 2A-2B. Vaporization occurs in the sump 322, and thus, sump 322 is integrated with a vaporizing chamber 302 instead of anesthetic vaporizer cartridge 300 including a separate sump that supplies the liquid anesthetic agent to the vaporizing chamber (e.g., via a pump). Similar to sump 222 of FIGS. 2A-2B, sump 322 includes a fill port (or neck) 327 that is factory sealed by a cap 323. Anesthetic vaporizer cartridge 300 may be delivered to a point of use pre-filled with liquid anesthetic agent 310 in sump 322 and may be completely sealed prior to installation in an anesthesia machine, as described above with respect to FIGS. 2A-2B.

Anesthetic vaporizer cartridge 300 may be a removable unit that is connected to and disconnected from gas passages of anesthesia machine 301 via a quick disconnect pneumatic system 382, which includes an input 384 and an output 386 and functions the same as quick disconnect pneumatic system 282 of FIGS. 2A-2B described above. Input 384 connects to a fresh gas flow from anesthesia machine 301 and enables fresh gas (e.g., oxygen, air, nitrous oxide, and combinations thereof) to flow from the anesthesia machine into vaporizing chamber 302 as carrier gas via a gas inlet passage 336. A heat pipe 330 extends within gas inlet passage 336 such that a wall defining gas inlet passage 336 is concentric around heat pipe 330. Further, gas inlet passage extends through an opening in housing 304 (which may include a liquid-tight seal, for example) and into sump 322 such that a first (e.g., top) portion of gas inlet passage 336 is external to sump 322 and a second (e.g., bottom) portion of gas inlet passage 336 is internal to sump 322 and configured to be at least partially submerged in the liquid anesthetic agent 310. Heat pipe 330 and gas inlet passage 336 do not directly contact each other, enabling the carrier gas to flow past heat pipe 330 within gas inlet passage 336 and into the liquid anesthetic agent 310 via a sparging filter 307, which is located near a bottom of sump 322 and is completely submerged within liquid anesthetic agent 310, to form a plurality of gas bubbles 312. Sparging filter 307 may cap the bottom of gas inlet passage 336, as shown, and may be comprised of metal or ceramic, for example. Sparging filter 307 may form a liquid-tight seal with the bottom surface of gas inlet passage 336 to allow gas to flow from gas inlet passage 336 to liquid anesthetic agent 310 while preventing the flow of liquid anesthetic agent 310 into gas inlet passage 336. The plurality of gas bubbles 312 pass through liquid anesthetic agent 310, becoming saturated with vaporized anesthetic agent, as they rise to the surface of the liquid.

Sparging filter 307 may increase an interfacial area between the carrier gas and liquid anesthetic agent 310 by decreasing a size of the gas bubbles 312, which in turn increases a rate of vaporization of liquid anesthetic agent 310. For example, gas bubbles 312 may be fine and/or micro bubbles. A geometry of sparging filter 307 may be selected to optimize an efficiency of the vaporization of the liquid anesthetic agent, which may be affected by the size of the gas bubbles 312 and the swirl of the gas bubbles 312, for example. In one embodiment, the size of the gas bubbles 312 may be selected to maximize the surface area of the fresh gas in contact with the liquid anesthetic agent 310 while reducing back pressure (e.g., a pressure drop across sparging filter 307) and to generate a defined and homogenous gas distribution. As an example, the large surface area-to-volume ratio of each small gas bubble 312 enables each gas bubble to become fully saturated with vapor of the liquid anesthetic agent 310.

Output 386 enables mixed gas comprising the carrier gas saturated with vaporized anesthetic agent to flow from vaporizing chamber 302 to the anesthesia machine via a gas outlet passage 338 (e.g., a vapor delivery passage). In one embodiment, output 386 may connect gas outlet passage 338 to a bypass gas flow of fresh gas at the anesthesia machine, and the mixed gas may flow into the bypass gas flow before being delivered to a patient. Together, gas inlet passage 336 and gas outlet passage 338 may form a manifold.

In the embodiment shown in FIG. 3, heat pipe 330 bends (e.g., by approximately)90° to enable heat pipe 330 to extend between a barrier 332 and gas inlet passage 336. Barrier 332 may form a gas-tight seal around the components disposed therein to isolate the components inside of barrier 332 from the components and environment outside of barrier 332. For example, barrier 332 may be a pneumatic barrier (e.g., a pneumatically sealed barrier) or may be hermetically sealed. In the embodiment shown in FIG. 3, a vertical portion of heat pipe 330 extends into gas inlet passage 336, while at least part of a horizontal portion of heat pipe 330 is isolated from vaporizing chamber 302 and gas inlet passage 336 via barrier 332. Further, the horizontal portion of heat pipe 330 crosses barrier 332 and extends into gas inlet passage 336 before the bend.

In the exemplary embodiment shown in FIG. 3, barrier 332 is located within anesthesia machine 301. For example, during installation of anesthetic vaporizer cartridge 300 into anesthesia machine 301, barrier 332 may be inserted into a compartment within anesthesia machine 301, and quick disconnect pneumatic system 382 may be connected to gas passages of anesthesia machine 301 to fluidically couple anesthesia machine gas flow to anesthetic vaporizer cartridge 300. Then, after use (or when sump 322 no longer holds enough liquid anesthetic agent 310 for completing a procedure), anesthetic vaporizer cartridge 300 may be disconnected from the anesthesia machine gas flow via quick disconnect pneumatic system 382, and barrier 332 may be removed from anesthesia machine 301. Anesthetic vaporizer cartridge 300 may then be returned to the manufacturer for refilling or refurbishing, and a different anesthetic vaporizer (holding the same or different liquid anesthetic agent at a same or different volume, depending on the next procedure to be performed) may be installed.

During operation, heat pipe 330 is heated via a heating element 308 and a ferromagnetic collar 306 positioned within barrier 332. Heat pipe 330 may be comprised of copper, for example, or another material having a high thermal conductivity (e.g., nickel plated copper). The horizontal portion of heat pipe 330, contained within barrier 332, may be in direct contact with ferromagnetic collar 306. In one embodiment, the horizontal portion of heat pipe 330 is friction-fit within ferromagnetic collar 306. Ferromagnetic collar 306 may be a thin-walled collar comprised of 600 series stainless steel, various grades of highly magnetic steel, iron, or other ferromagnetic materials. Heating element 308 is positioned within barrier 332, external to vaporizing chamber 302, and may be coiled around a length of ferromagnetic collar 306, as shown. Further, heating element 308 may be in direct contact with (e.g., touching) ferromagnetic collar 306 or may not be in direct contact with ferromagnetic collar 306.

In the embodiment of FIG. 3, heating element 308 is an inductive heater including a power source, a high-current inductive heating coil, and an electronic oscillator that passes a high frequency (e.g., ~50 kHz) alternating current through the coil, creating a rapidly alternating magnetic field. The rapidly alternating magnetic field produced by heating element 308 penetrates ferromagnetic collar 306, generating eddy currents within ferromagnetic collar 306 to heat it via Joule heating and magnetic hysteresis losses. In this way, heating element 308 may selectively heat ferromagnetic collar 306 via induction heating without becoming hot itself and/or without directly heating additional components of anesthetic vaporizer cartridge 300 (e.g., heat pipe 330).

Induction heating of ferromagnetic collar 306 by heating element 308 may provide several advantages. For example, the heat is generated inside the ferromagnetic collar itself instead of via an external heat source (e.g., via conduction). In this way, ferromagnetic collar 306 may be rapidly heated once heating element 308 is activated. Further, heating element 308 need not be in direct contact with ferromagnetic collar 306, reducing contamination between components. However, in other embodiments, heating element 308 may heat through conduction, and thus heating element 308 may be in direct contact with ferromagnetic collar 306 for efficient heat transfer.

As heat is generated within ferromagnetic collar 306 during the induction heating, the heat may be efficiently transferred to heat pipe 330 via conduction. Thus, selectively heating ferromagnetic collar 306 via induction heating by heating element 308 may also selectively heat the heat pipe 330. Heat pipe 330 transports the generated heat along its length such that a temperature of the entire heat pipe is substantially the same, and the temperature of the heat pipe is substantially the same as a temperature of ferromagnetic collar 306. Heat transfers from the hot heat pipe 330 to the colder carrier gas flowing past heat pipe 330. By activating heating element 308 to heat ferromagnetic collar 306 and thus heat pipe 330, the latent heat of vaporization for the phase transition from the liquid form of the anesthetic agent to the vapor form may be provided. Thus, all of the carrier gas that flows through vaporizing chamber 302 via gas inlet passage 336 may be fully saturated with vapor from liquid anesthetic agent 310, even at high fresh gas flow rates (e.g., 10 L/min).

Output 386 enables mixed gas comprising the carrier gas saturated with vaporized anesthetic agent to flow from vaporizing chamber 302 to anesthesia machine 301 via a gas outlet passage 338 (e.g., a vapor delivery passage). In one embodiment, output 386 may connect gas outlet passage 338 to a bypass gas flow of fresh gas at anesthesia machine 301, and the mixed gas may flow into the bypass gas flow before being delivered to a patient.

An electrical connector 380 may electronically couple heating element 308 to a power source 331 and/or a controller 325, as described above with respect to electrical connector 280, power source 231, and controller 225 of FIGS. 2A and 2B. As shown, electrical connector 380 may include a terminal positioned exterior to barrier 332 and wires 388 that extend into barrier 332 to form a permanent electrical connection with heating element 308. In other embodiments, power source 331 may be integrated in the disposable anesthetic vaporizer cartridge 300 unit and positioned within barrier 332. In some embodiments, a temperature sensor 328 for measuring a temperature of heat pipe 330 may be positioned within barrier 332 and may also be electronically coupled to controller 325 via electrical connector 380. In another embodiment, anesthetic vaporizer cartridge 300, particularly heating element 308, may be wirelessly connected to controller 325. Controller 325 may function similarly to controller 225 described above with respect to FIGS. 2A-2B, such as to adjust the amount of power supplied to heating element 308 to adjust the concentration or flow rate of vaporized anesthetic agent produced, and may receive operator input via an HMI 326. In particular, controller 325 may receive an electronic feedback signal from temperature sensor 328 regarding the temperature of heat pipe 330 (which may be substantially the same temperature as ferromagnetic collar 306), process the input data, and adjust operation of heating element 308 based on the received signal and instructions stored on a memory of the controller. In still another embodiment, anesthetic vaporizer cartridge 300 may be manually controlled by the operator (e.g., via a dial) instead of being electronically controlled by controller 325, as also described above with respect to FIGS. 2A-2B.

Barrier 332 may form a gas-tight seal around the components disposed therein to isolate the components inside of barrier 332 from the components and environment outside of barrier 332. In other embodiments, heat pipe 330 may extend into sump 322 at other locations, such as through the bottom of housing 304 or a side of housing 304. Thus, the positioning shown in FIG. 3 of heat pipe 330, barrier 332, and the other components disposed within barrier 332 relative to sump 322 is provided by way of example. In particular, by housing temperature sensor 328 and heating element 308 within barrier 332, electronic components of anesthetic vaporizer cartridge 300 may be isolated, such as via pneumatic separation, from a potentially oxygen-enriched environment that may form within and around anesthetic vaporizer cartridge 300. For example, the fresh gas flow may include oxygen gas at a higher concentration than air. Over time, pneumatic (e.g., gas-tight) seals within anesthetic vaporizer cartridge 300 may degrade, allowing the oxygen-enriched gas supplied from the fresh gas flow to leak out of the various gas delivery passages. By sealing the electronic components in the barrier, any electrical sparking or excessive heating (e.g., due to degradation of heating element 308) will not occur in the oxygen-enriched environment, reducing further degradation of the anesthetic vaporizer.

Other disposable anesthetic vaporizer cartridge configurations that use an inductively heated heat pipe are also possible. Turning now to FIG. 4, a third exemplary embodiment of an anesthetic vaporizer cartridge 400 is shown, which may be installed in an anesthesia machine 401 (which may represent anesthesia machine 100 shown in FIG. 1, for example). As one example, anesthetic vaporizer cartridge 400 may be anesthetic vaporizer 114 of FIG. 1. Anesthetic vaporizer cartridge 400 may be similar to anesthetic vaporizer 300 of FIG. 3, including a heat pipe 430 and a barrier 432, but anesthetic vaporizer cartridge 400 does not utilize a bubble-through architecture.

Anesthetic vaporizer cartridge 400 includes a housing 404 that divides a sump 422 from barrier 432. Sump 422 stores a liquid anesthetic agent 410 therein, which may be similar to liquid anesthetic agent 210 of FIGS. 2A-2B. Vaporization occurs in the sump 422, and thus, the sump 422 is integrated into a vaporizing chamber 402. Sump 422 includes a fill port (or neck) 427 that is sealed by a cap 423. Anesthetic vaporizer cartridge 400 may be delivered to a point of use (e.g., a hospital or other healthcare facility) pre-filled with liquid anesthetic agent 410 in sump 422, and thus, sump 422 may be sealed by cap 423 by an agent manufacturer, such as described above with respect to FIGS. 2A-2B.

Anesthetic vaporizer cartridge 400 may be a removable unit that is connected to and disconnected from gas passages of anesthesia machine 401 via a quick disconnect pneumatic system 482, which includes an input 484 and an output 486. Input 484 connects to a fresh gas flow from the anesthesia machine and, when connected, enables fresh gas (e.g., oxygen, air, nitrous oxide, and combinations thereof) to flow from the anesthesia machine to anesthetic vaporizer 300 via a gas inlet passage 436. Output 486 connects to a mixed gas flow of the anesthesia machine and, when connected, enables mixed gas (containing both fresh gas and anesthetic agent vapor 212) to flow from anesthetic vaporizer cartridge 400 to anesthesia machine 401 via a manifold 454 and a gas outlet passage 438, as will be elaborated below.

In the embodiment shown in FIG. 4, housing 404 comprises a gas generation passage 405 that extends into sump 422. Gas generation passage 405 is capped by a manifold 454 that is attached to sump 422 via a plurality of fasteners 455 (which may be screws or bolts, for example). Thus, manifold 454 may be removable from sump 422 while forming a gas-tight seal with sump 422 when attached. Further, in the embodiment shown in FIG. 4, heat pipe 430 is bent (e.g., by approximately)90° so that a vertical portion of heat pipe 430 extends through an opening in housing 404 (which may include a liquid-tight seal, for example) and into sump 422, while a horizontal portion of heat pipe is isolated from sump 422 (and vaporizing chamber 402) via barrier 432. For example, the vertical portion of heat pipe 430 crosses barrier 432 and into liquid anesthetic agent 410 within sump 422 via a top wall of barrier 432 and a bottom wall of sump 422. Further, the vertical portion of heat pipe 430 extends into gas generation passage 405. For example, gas generation passage 405 may be concentric around heat pipe 430, and gas generation passage 405 does not extend to the bottom of sump 422, allowing liquid anesthetic agent 410 to flow into gas generation 405.

Heat pipe 430 is configured to be submerged in liquid anesthetic agent 410 within sump 422, particularly within gas generation passage 405, such that heat pipe 430 may be in direct contact with liquid anesthetic agent 410 within gas generation passage 405. During operation, heat pipe 430 is heated via a heating element 408 and a ferromagnetic collar 406 positioned within barrier 432, which function similarly to heating element 308, ferromagnetic collar 306, and barrier 332 described above with respect to FIG. 3. Heat transfers from the hot heat pipe 430 to the colder liquid anesthetic agent 410 within sump 422, and particularly within gas generation passage 405. By activating heating element 408 to heat ferromagnetic collar 406, and thus heat pipe 430, the latent heat of vaporization for the phase transition from the liquid form of the anesthetic agent to the vapor form may be provided. For example, localized boiling may occur in the liquid anesthetic agent 410 proximal to heat pipe 430, such as within gas generation passage 405, resulting in anesthetic agent vapor 412. This localized boiling may be more efficient than bulk-boiling the liquid anesthetic agent 410 within sump 422. Gas generation passage 405 then directs the anesthetic agent vapor 412 to manifold 454. Further, heat pipe 430 may at least partially extend within manifold 454 to heat manifold 454 and reduce or prevent vapor condensation within manifold 454.

The evolved anesthetic agent vapor 412 (e.g., vaporized anesthetic agent) may exit vaporizing chamber 402 via a vapor delivery passage 440 coupled to outlet manifold 454 and flow to a venturi 460. An inlet of venturi 460 is coupled to gas inlet passage 436, through which fresh gas flow is provided to venturi 460, and an outlet of venturi 460 is coupled to gas outlet passage 438. The fresh gas flow may be provided via one or more gas pipelines (e.g., via pipeline connections 146 shown in FIG. 1) and/or one or more gas-holding cylinders (e.g., gas-holding cylinder 148 of FIG. 1). Venturi 460 includes a tapered tube 462 having a throat region 464 and functions similarly to venturi 260, tapered tube 262, and throat region 264 described above with respect to FIGS. 2A-2B. As the fresh gas flows through tapered tube 462, a pressure drop occurs at throat region 464 that pulls the anesthetic agent vapor 412 into the fresh gas stream, resulting in mixed gas containing both the fresh gas from the fresh gas flow and the anesthetic agent vapor 412. The mixed gas may then be delivered to the patient via an inspiratory limb of a breathing circuit of anesthesia machine 401 (e.g., via inspiratory port 118 described with respect to FIG. 1) via gas outlet passage 438 and output 486.

An electronic connection 480 may electronically couple heating element 408 to a controller 425. Controller 425 may be a dedicated controller of anesthetic vaporizer cartridge 400 or may be a controller of the anesthesia machine 401 (e.g., controller 140 shown in FIG. 1). Thus, controller 425 may not be included in the disposable anesthetic agent cartridge of anesthetic vaporizer cartridge 400. In some embodiments, electronic connection 480 may also electronically couple heating element 408 to a power source 431, or power source 431 may be part of anesthetic vaporizer cartridge 400 and disposed within barrier 432. When power source 431 is included in anesthetic vaporizer cartridge 400, power source 431 may be a disposable or rechargeable battery, for example. In some embodiments, a temperature sensor 428 for measuring a temperature of heat pipe 430 may be disposed within barrier 432 and may also be electronically coupled to controller 425 via electronic connection 480. Controller 425 may function similarly to controller 225 described above with respect to FIG. 2, such as to adjust the amount of power supplied to heating element 408 to adjust the concentration or flow rate of vaporized anesthetic agent produced, and may receive operator input via an input device 426. In another embodiment, anesthetic vaporizer cartridge 400, particularly heating element 408, may be wirelessly connected to controller 425. In still another embodiment, anesthetic vaporizer cartridge 400 may be manually controlled by the operator (e.g., via a dial) instead of being electronically controlled by controller 425.

Prior to use, anesthetic vaporizer cartridge 400 may be installed in anesthesia machine 401 by fluidically coupling anesthesia machine gas flow to anesthetic vaporizer cartridge 400 via quick disconnect pneumatic system 482 and electronically coupling anesthetic vaporizer cartridge 400 to controller 425 (and/or power source 431) via the electronic connection 480. Then, after use (or when sump 422 no longer holds enough liquid anesthetic agent 410 for completing a procedure), anesthetic vaporizer cartridge 400 may be disconnected from the anesthesia machine gas flow via quick disconnect pneumatic system 482 and disconnected from controller 425 via electronic connection 480. Anesthetic vaporizer cartridge 400 may then be returned to the manufacturer for refilling or refurbishing, and a different anesthetic vaporizer (holding the same or different liquid anesthetic agent at a same or different volume, depending on the next procedure to be performed) may be installed in anesthesia machine 401.

Turning now to FIG. 5, an exemplary embodiment of an anesthetic agent fill level sensing system 500 is shown. Anesthetic agent fill level sensing system 500 includes an anesthesia machine 501 (which may be anesthesia machine 100 introduced in FIG. 1, for example) and an anesthetic vaporizer cartridge 502. As an example, anesthetic vaporizer cartridge 502 may be anesthetic vaporizer cartridge 200 of FIGS. 2A and 2B, anesthetic vaporizer cartridge 300 of FIG. 3, or anesthetic vaporizer cartridge 400 of FIG. 4. In particular, anesthetic vaporizer cartridge 502 is installed within (e.g., mated with) anesthesia machine 501 for delivering anesthetic agent vaporized within anesthetic vaporizer cartridge 502 to a patient via anesthesia machine 501, as elaborated above with particular reference to FIGS. 2A-2B, and so anesthesia machine 501 may be referred to herein as the mating anesthesia machine.

In the embodiment shown in FIG. 5, anesthetic vaporizer cartridge 502 includes a housing 504 and a window 506 coupled within housing 504. As described above with respect to FIGS. 2A-2B, housing 504 may define a sump 522 that contains a liquid anesthetic agent 510 therein. Window 506 is comprised of an optically transparent material, whereas housing 504 may be opaque. Further, window 506 may be anti-reflective. Thus, the liquid anesthetic agent 510 contained within sump 522 of anesthetic agent cartridge 502 is visible via window 506 but may not be visible through housing 504, at least in some embodiments. Further, window 506 may form a liquid- and gas-tight seal with housing 504.

Window 506 may be positioned on a side of sump 522 and may extend along a length of housing 504. In the embodiment shown in FIG. 5, window 506 extends from a top surface of sump 522 (with respect to gravity and with respect to the page) to a bottom surface of sump 522 so that window 506 provides a view of liquid anesthetic agent 510 within sump 522 at any fill level (e.g., from completely full to completely empty). However, other configurations are also possible, such as where window 506 provides a view of liquid anesthetic agent 510 within a bottom half of sump 522, for example.

Window 506 is positioned on sump 522 such that, when anesthetic vaporizer cartridge 502 is installed in anesthesia machine 501, an interface 508 forms between window 506 and a plurality of optical sensors 512 included in anesthesia machine 501. The plurality of optical sensors 512 may be reflective optical sensors that are vertically aligned along a common axis and arranged along interface 508, from top to bottom, such that the plurality of optical sensors 512 span the length of window 506. In the example shown, the plurality of optical sensors 512 include discrete, individual optical sensors 512a, 512b, 512c, 512d, 512e, 512f, 512g, 512h, 512i, and 512k that each emit a light signal 514 (only one of which is labeled) and are each configured to detect a reflection signal 516 (only one of which is labeled). Although the example embodiment shown in FIG. 5 includes ten optical sensors, it may be understood that other numbers of optical sensors are also possible (e.g., more than ten or less than ten).

Specifically, each of the plurality of optical sensors 512 may include a light source for producing the light signal 514 (such as a visible or infrared light-emitting diode) and a light detector (e.g., a phototransitor) for sensing the presence or absence of the reflection signal 516, which travels in the opposite direction of light signal 514. For example, the light signal 514 may be visible or infrared light at a discrete wavelength (or wavelength range) that travels in a first direction and has a first intensity, and the reflection signal may be visible or infrared light at the same wavelength (or wavelength range) that travels in a second direction, opposite to the first direction, and has a second, lower intensity.

The light signal 514 emitted by each optical sensor may pass through window 506 due to its optical transparency (but may not pass through housing 504, for example). Reflection occurs at an interface between two different media (e.g., each having a different index of refraction). When the light signal 514 travels through an air gap at interface 508 to vapor (e.g., air, medical gas, and/or vaporized anesthetic agent) within sump 522, reflection does not occur (or is too small to be detected). Thus, when a level of anesthetic agent 510 in sump 522 is lower than the light signal 514 emitted by a particular optical sensor, no reflection signal 516 is produced. In contrast, when the level of liquid anesthetic agent 510 in sump 522 is higher than or overlaps with the light signal 514 emitted by a particular optical sensor, the liquid anesthetic agent 510 reflects a portion of the light from light signal 514 back to the corresponding optical sensor as reflection signal 516.

Each of the individual optical sensors is positioned at a different, non-overlapping vertical location such that the light signal 514 emitted by one optical sensor does not overlap with the light signal of an adjacent optical sensor. Further, the reflection signal 516 resulting from the light signal from one optical sensor is not received by an adjacent optical sensor.

A controller (e.g., of anesthesia machine 501) may receive an output from each of the plurality of optical sensors 512 corresponding to the presence or absence of a received reflection signal 516 and may further associate each optical sensor with a discrete fill level of liquid anesthetic agent 510 within sump 522. In the example shown in FIG. 5, optical sensors 512a, 512b, 512c, 512d, 512e, and 512f each emit a light signal 514 and do not receive a reflection signal, whereas optical sensors 512*g*, 512*h*, 512*i*, and 512*j* each emit a light signal 514 and receive a reflection signal 516. Thus, the controller may determine that the level of liquid anesthetic agent 510 is between optical sensor 512*f* and optical sensor 512*g* and may accordingly assign a discrete fill level (such as a volume, height, percentage capacity, etc.) associated with optical sensor 512*g* to liquid anesthetic agent 510. The assigned fill level may be output to an operator of anesthesia machine 501 (e.g., via a display) and/or may be used for determining when to replace anesthetic vaporizer cartridge 502, as will be elaborated below.

Next, FIG. 6 shows an exemplary embodiment of a method 600 for prompting replacement of an empty anesthetic vaporizer cartridge installed in an anesthesia machine. The anesthetic vaporizer cartridge may be one of the anesthetic vaporizer cartridges shown FIGS. 2A-2B, 3, and 4, for example, and the anesthesia machine may be anesthesia machine 100 shown in FIG. 1. As one example, method 600 may be executed by a controller (e.g., controller 225 of FIGS. 2A-2B, controller 325 of FIG. 3, or controller 425 of FIG. 4) according to instructions stored in a memory of the controller and in conjunction with one or more inputs, such as inputs received from an operator via a human-machine interface (e.g., HMI 226 of FIGS. 2A-2B, HMI 326 of FIG. 3, of HMI 426 of FIG. 4). Further, the controller may output information to an operator of the anesthesia machine via the human-machine interface.

Anesthetic vaporizer cartridge information is received at 602. For example, the anesthetic vaporizer cartridge information may include the type of anesthetic agent contained in the anesthetic vaporizer cartridge (e.g., desflurane, isoflurane, sevoflurane, or the like) and a starting (e.g., initial) volume of liquid anesthetic agent in the anesthetic vaporizer cartridge. In some examples, the anesthetic vaporizer cartridge information may further include specific identification information, such as a unique serial number of the anesthetic vaporizer cartridge. When the anesthetic vaporizer cartridge has not yet been used, the starting volume of the liquid anesthetic agent may be equal to a volume capacity of the sump. When the anesthetic vaporizer cartridge has already been used, the starting volume for the current procedure may be determined based on the volume capacity of the sump and a tracked usage amount, which will be further described below, and/or a currently measured level (e.g., when a level sensor or a fill level sensing system is included, such as shown in FIG. 5). In one embodiment, the operator may manually enter the anesthetic vaporizer cartridge information via the human-machine interface. In another embodiment, at least some of the anesthetic vaporizer cartridge information may be auto-populated based on the serial number, which may be manually entered by the operator or scanned via the HMI (e.g., via a camera). In still another embodiment, the anesthetic vaporizer cartridge information may be received from a non-volatile memory of the anesthetic vaporizer cartridge (e.g., EEPROM) via a communications bus (e.g., contact pads 246 shown in FIG. 2B).

Anesthetic agent usage (e.g., consumption) is tracked during operation based on delivery settings and/or sensor output at 604. For example, in order to supply a desired amount of anesthetic agent to the patient, the controller may receive an anesthetic agent concentration setpoint from the operator and supply a corresponding amount of power to a heating element in order to provide vaporized anesthetic agent at the anesthetic agent concentration setpoint, as will be further described below with respect to FIG. 7. Further, the controller may receive a fresh gas flow rate indicative of the flow rate of the fresh gas into the anesthetic vaporizer cartridge from the operator. Thus, the delivery settings include the anesthetic agent concentration setpoint and the fresh gas flow rate. In one embodiment, the controller may calculate a consumed volume and/or usage rate of the anesthetic agent (e.g., the consumed volume per unit of time) based on the anesthetic agent concentration setpoint, the fresh gas flow rate, and the type of anesthetic agent, such as by inputting the anesthetic agent concentration setpoint, the fresh gas flow rate, and the type of anesthetic agent into one or more look-up tables, algorithms, or equations. Additionally or alternatively, the controller may track anesthetic agent usage based on measured anesthetic agent levels received from the level sensor or fill level sensing system. The controller may also track an amount of time (e.g., duration) that the anesthetic vaporizer cartridge has been operated to supply anesthetic agent during the current procedure. In general, as the anesthetic agent concentration setpoint increases, the anesthetic agent usage rate increases.

As one example, the controller may calculate the consumed volume using the following equations:

$$\text{Saturated\_Gas\_Volume} = \frac{SW \cdot GC \cdot (273 + T)}{MW \cdot 273} \quad \text{(Equation 1)}$$

$$\text{Agent\_Consumption} = \frac{\text{Ave\_FGF} \cdot \text{Ave\_Agent\_Conc} \cdot \text{Duration}}{\text{Saturated\_Gas\_Volume} \cdot 100} \quad \text{(Equation 2)}$$

Equation 1 results in the term Saturated_Gas_Volume (in milliliters, mL), which corresponds to an amount of vaporized anesthetic agent produced at a given temperature (T) of the anesthetic agent for the type of anesthetic agent being used. The term SW is the specific weight of the anesthetic agent in g/mL, which is selected based on the type of anesthetic agent being used (e.g., 1.49 g/mL for isoflurane, 1.53 g/mL for sevoflurane, or 1.47 g/mL for desflurane). For example, the controller may input the type of anesthetic agent into a look-up table, which may output the specific weight of the given type of anesthetic agent. The term GC is Avogadro's gas constant, which is a universal constant for all gases (e.g., independent of the type of anesthetic agent being used) that defines that at standard conditions for temperature and pressure, dry (e.g., STPD, corresponding to a temperature of 273 K and a pressure of 1 atmosphere, without water vapor), one mole of any gas contains $6.022 \times 10^{23}$ molecules, which occupy a volume of 22,400 mL. The term MW is the molecular weight of the anesthetic agent being used in g/mol, which is selected based on the type of anesthetic agent being used (e.g., 184 g/mol for isoflurane, 200 g/mol for sevoflurane, or 168 g/mol for desflurane). For example, the controller may input the type of anesthetic agent into a separate look-up table, which may output the molecular weight of the given type of anesthetic agent.

The Saturated_Gas_Volume calculated via Equation 1 may be used in Equation 2 to determine Agent_Consumption (in mL), which corresponds to the volume of anesthetic agent used during the current procedure. In Equation 2, the term Ave_FGF is the average fresh gas flow rate (in mL/min) during the current procedure, the term Ave_Agent_Conc is the average anesthetic agent concentration setpoint during the current procedure (in % volume), and the term Duration is the duration that the anesthetic vaporizer cartridge has been operated during the current procedure.

A remaining anesthetic agent volume in the anesthetic vaporizer cartridge is determined based on the tracked usage at 606. For example, the controller may estimate the volume of anesthetic agent consumed during the current operation of the anesthetic vaporizer cartridge in real-time and subtract the estimated amount of anesthetic agent consumed from the starting volume. In some embodiments, the controller may output the remaining anesthetic agent volume to the operator, such as via the HMI.

It is determined if the remaining anesthetic agent volume is less than a threshold volume at 608. The threshold volume may be non-zero volume that is pre-calibrated to prevent the anesthetic agent from being completely depleted from the sump during usage, thereby enabling the anesthetic vaporizer cartridge to be replaced before an empty status is reached.

If the remaining anesthetic agent volume is less than the threshold volume, method 600 proceeds to 610, and an alert for anesthetic agent cartridge replacement is output. For example, the controller may communicate the replacement alert to the operator via the human-machine interface. In one embodiment, the replacement alert may include an audible alarm or message. In another embodiment, the replacement alert may additionally or alternatively include a visual message. The message may include an indication that anesthetic agent cartridge replacement is needed as well as the determined remaining anesthetic agent volume in the anesthetic vaporizer cartridge. Further, in some embodiments, the controller may prevent the anesthetic vaporizer cartridge from being operated, such as by disabling a heating element of the anesthetic vaporizer cartridge when the anesthesia machine is not actively being used to supply anesthetic agent to a patient. In this way, the anesthesia machine may not be operated when the volume of anesthetic agent in the anesthetic vaporizer cartridge is insufficient for completing a procedure. Method 600 may then return.

If instead the remaining anesthetic agent volume is not less than the threshold volume, method 600 proceeds to 612, and anesthetic agent usage continues to be tracked at 612. Continue to track the anesthetic agent usage may include tracking the anesthetic agent usage during a single usage event (e.g., when the anesthetic vaporizer cartridge is designed to supply anesthetic agent for a single procedure before being refilled or disposed of) or across multiple usage events (e.g., when the anesthetic vaporizer cartridge is to supply anesthetic agent for multiple procedures before being refilled or disposed of). For example, the controller may program the non-volatile memory integral to the anesthetic vaporizer cartridge with the remaining volume of anesthetic agent at the end of the procedure. Therefore, if the anesthetic vaporizer cartridge is removed and installed in a different anesthesia machine, the new anesthesia machine may receive the current volume of liquid anesthetic agent in the sump from the non-volatile memory of the anesthetic vaporizer cartridge upon installation. Method 600 may then return.

Figure 7:
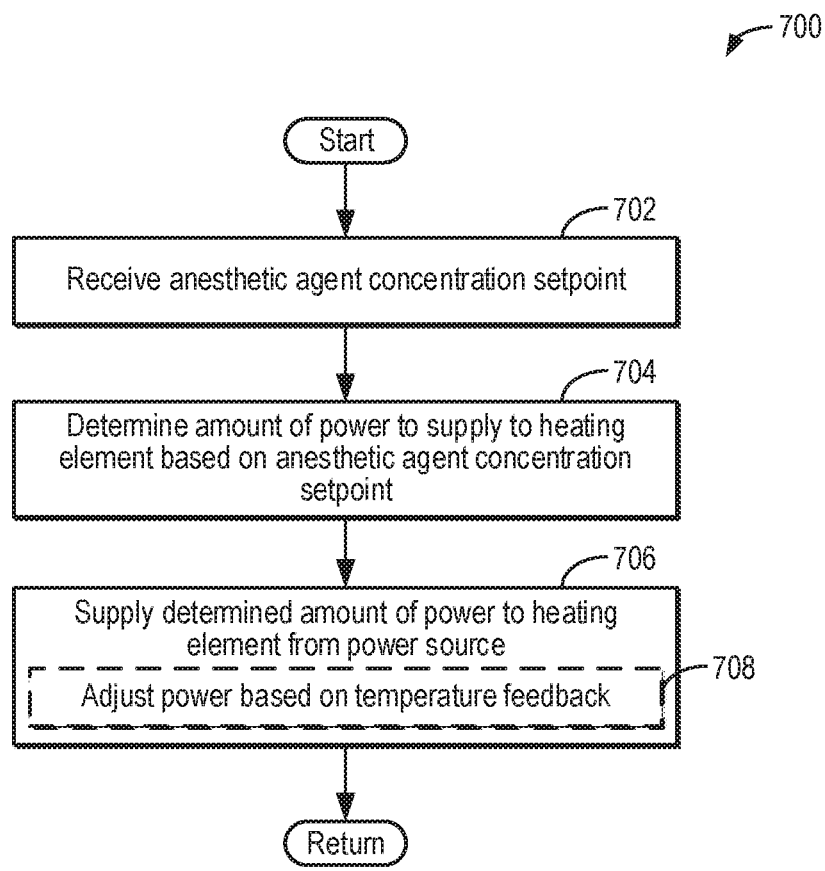
FIG. 7 is a flow chart illustrating an exemplary embodiment of a method for controlling an amount of power supplied to a heating element of an anesthetic vaporizer cartridge.

Turning now to FIG. 7, an embodiment of an example method 700 for operating a heating element of an anesthetic vaporizer cartridge, such as the anesthetic vaporizer cartridges of FIGS. 2A-2B, 3, and 4, is shown. As one example, method 700 may be executed by a controller (e.g., controller 225 of FIGS. 2A-2B, controller 325 of FIG. 3, or controller 425 o FIG. 4) in order to facilitate vaporization of a liquid anesthetic agent according to instructions stored in a memory of the controller and in conjunction with one or more inputs (e.g., HMI 226 of FIGS. 2A-2B, HMI 326 of FIG. 3, of HMI 426 of FIG. 4) and actuators (e.g., heating element 208 of FIG. 2B, heating element 308 of FIG. 3, or heating element 408 of FIG. 4). The heating element may be a conductive heating coil configured to heat a vaporization zone of a capillary pump (as described above with respect to FIGS. 2A-2B) or an inductive heating coil configured to heat a ferromagnetic collar and a heat pipe (as described above with respect to FIGS. 3 and 4), for example. Adjusting the amount of heat generated via the heating element may adjust an amount of anesthetic agent output by the anesthetic vaporizer and thus, in one embodiment, method 700 may be used to control the amount of anesthetic agent output by the anesthetic vaporizer to a patient breathing circuit. In other embodiments, method 700 may be performed in conjunction with additional methods, such as valve control methods, to control the amount of anesthetic agent output by the anesthetic vaporizer.

At 702, an anesthetic agent concentration setpoint is received. The anesthetic agent may be any suitable volatile liquid anesthetic agent, such as desflurane, isoflurane, sevoflurane, or the like, or another medication that may be nebulized/inhaled, such as albuterol. The anesthetic agent concentration setpoint may be a percentage of the vaporized anesthetic agent per volume of a fresh gas/vaporized anesthetic agent mix provided to a patient. The anesthetic agent concentration setpoint, and, in some examples, the type of anesthetic agent used, may be obtained via user input to the controller (e.g., via the input device) or via another suitable mechanism.

At 704, an amount of power to supply to the heating element is determined based on the anesthetic agent concentration setpoint. The heating element may include a variable frequency drive to vary the heating element voltage (or current) and frequency, such as via pulse-width modulation (PWM). In one embodiment, the controller may determine a drive voltage and frequency (or duty cycle of voltage) to supply to the heating element by inputting the anesthetic agent concentration setpoint into a look-up table, algorithm, or map, which may output the corresponding drive voltage and frequency (or duty cycle of voltage) to provide anesthetic agent at the anesthetic agent concentration setpoint. For example, during manufacturing, the amount (e.g., concentration or flow rate) of anesthetic agent vapor produced at different power amounts may be measured via a concentration sensor such that heater power versus anesthetic agent output is mapped. These data may be used to generate a look-up table, which may be stored in the memory of the controller. Then, during operation of the anesthetic vaporizer, the controller may access the pre-mapped values stored in the look-up table to determine the amount power to supply to the heating element without performing additional modeling or calculations, thereby decreasing an amount of processing power needed by the controller to control the heating element (and thus the amount of anesthetic agent output by the anesthetic vaporizer).

At 706, the determined amount of power is supplied to the heating element from a power source. In one embodiment, the power source (e.g., power source 231 of FIGS. 2A and 2B, power source 331 of FIG. 3, or power source 431 of FIG. 4) is external to the anesthetic vaporizer and electrically coupled to the heating element, which is internal to the anesthetic vaporizer, via a disconnectable mating component. The controller may actuate the power source to supply the heating element with power at the determined drive voltage and frequency (or duty cycle of voltage). For example, the amount of power supplied to the heating element from the power source, such as the drive voltage and frequency (or duty cycle of voltage) at which the heating element is operated, may be higher when the anesthetic agent concentration setpoint is higher and lower when the anesthetic agent concentration setpoint is lower.

In some embodiments, the amount of power supplied to the heating element is adjusted based on temperature feedback, as optionally indicated at 708. For example, the controller may receive a measured temperature from a temperature sensor coupled within the anesthetic vaporizer, such as temperature sensor 228 of FIG. 2B, temperature sensor 328 of FIG. 3, or temperature sensor 428 of FIG. 4. In such embodiments, the controller may additionally associate a target temperature value with the amount of power to supply to the heating element for the input anesthetic agent concentration setpoint (e.g., in the look-up table, algorithm, or map described above at 704). In one embodiment, the controller may include a proportional-integral-derivative controller that determines an error value between the target temperature and the measured temperature based on proportional, integral, and derivative terms. In another embodiment, the controller may directly compare the measured temperature to the target temperature. If the measured temperature is greater than the target temperature (e.g., if the error value indicates that the measured temperature is greater than the target temperature), the power supplied to the heating element may be decreased. For example, the controller may decrease the drive voltage and frequency (or duty cycle of voltage) supplied to the heating element from the power source responsive to the measured temperature being greater than the target temperature in order to decrease the measured temperature to the target temperature. If the measured temperature is less than the target temperature (e.g., if the error value indicates that the measured temperature is less than the target temperature), the power supplied to the heating element may be increased. For example, the controller may increase the drive voltage and frequency (or duty cycle of voltage) supplied to the heating element from the power source responsive to the measured temperature being less than the target temperature in order to increase the measured temperature to the target temperature. However, in other embodiments, the controller may not use temperature feedback to control the power supplied to the heating element, and 708 may be omitted.

Method 700 may return so that the power supplied to the heating element may be adjusted as the anesthetic agent concentration setpoint changes until the system is deactivated and anesthetic agent is no longer supplied to the patient. For example, the controller may increase the power supplied to the heating element responsive to the anesthetic agent concentration setpoint increasing and decrease the power supplied to the heating element as the anesthetic agent concentration setpoint decreases. In this way, vaporized anesthetic agent may be provided using a simple control scheme, further decreasing anesthetic vaporizer costs.

Thus, the systems and methods described herein provide for a single use or reusable cartridge-style anesthetic vaporizer system. In some embodiments, the anesthetic vaporizer system may be a wick-based anesthetic vaporizer including a capillary pump, wherein heating the capillary pump heats liquid anesthetic drawn up the wick to facilitate vaporization. In other embodiments, the anesthetic vaporizer system may be a bubble-through anesthetic vaporizer, wherein carrier gas bubbles and liquid anesthetic agent are heated by a heat pipe friction fit within an inductively heated ferromagnetic collar to provide latent heat of vaporization and increase the saturation of the carrier gas with anesthetic agent vapor. In still other embodiments, the heat pipe may locally heat the liquid anesthetic agent within a gas generation passage. By heating anesthetic vaporizer components, a quicker response time may be provided than bulk boiling the anesthetic agent, and a smaller amount of energy may be consumed. Further, high concentrations of anesthetic agent at high flow rates may be maintained with high accuracy and simplified heater control. Further still, by providing the anesthetic vaporizer as a limited use, self-contained cartridge, costs associated with anesthetic vaporizer ownership and maintenance may be decreased while anesthetic vaporizer portability is increased. Additionally, operator and environmental exposure to anesthetic agent may be decreased by providing the sump pre-filled and having larger volume capacities.

A technical effect of a cartridge-style disposable anesthetic vaporizer is that the anesthetic vaporizer may be a self-contained unit that may be manufactured at decreased cost while reducing clinician exposure to anesthetic agent.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for an anesthetic vaporizer cartridge, comprising:
   a housing defining a sump, the sump configured to hold a self-contained supply of liquid anesthetic agent;
   a heating element electrically coupled to an electrical mating component;
   a gas inlet passage and a gas outlet passage;
   a manifold fluidically coupled to the gas inlet passage and the gas outlet passage, the manifold coupled to the housing and forming a gas-tight seal with the sump; and
   a quick disconnect pneumatic system coupled to the gas inlet passage and the gas outlet passage, sealing the gas inlet passage and the gas outlet passage from atmosphere.

2. The system of claim 1, further comprising a capillary pump, the capillary pump including a vaporization zone housed within the manifold and a wick extending into the sump and configured to be submerged in the liquid anesthetic agent in the sump.

3. The system of claim 2, wherein the heating element is housed within the manifold and is positioned in direct contact with the vaporization zone, and the electrical mating component includes a terminal external to the manifold and wires that extend from the terminal to the interior of the manifold.

4. The system of claim 2, further comprising a vapor delivery passage that fluidically couples the manifold to a throat region of a venturi, an inlet of the venturi coupled to the gas inlet passage and an outlet of the venturi coupled to the gas outlet passage.

5. The system of claim 1, wherein the housing further defines a gas-tight barrier, the gas-tight barrier separated from the sump by the housing, and the heating element is housed within the gas-tight barrier.

6. The system of claim 5, further comprising a heat pipe, a first portion of the heat pipe housed within the gas-tight barrier and a second portion of the heat pipe crossing the barrier and extending into the sump.

7. The system of claim 6, further comprising a ferromagnetic collar in direct contact with the first portion of the heat pipe, the ferromagnetic collar housed within the gas-tight barrier, and wherein the heating element is an inductive heating element.

8. The system of claim 6, wherein the second portion of the heat pipe extends into a gas generation passage and is configured to be at least partially submerged in the liquid anesthetic agent, and the gas generation passage is concentric around the heat pipe.

9. The system of claim 6, wherein a portion of the gas inlet passage extends into the sump.

10. The system of claim 9, further comprising a sparging filter coupled to the portion of the gas inlet passage, the sparging filter forming a liquid-tight seal with the portion of the gas inlet passage, and wherein second portion of the heat pipe extends into the gas inlet passage and the gas inlet passage is concentric around the heat pipe.

11. A system for an anesthetic vaporizer, comprising:
a self-contained cartridge, the self-contained cartridge including:
a sump integrated with a vaporizing chamber, the sump storing an anesthetic agent within a housing;
a gas inlet passage fluidically coupled to the vaporizing chamber and configured to be coupled to a supply of medical gas via a pneumatic quick disconnect input;
a gas outlet passage fluidically coupled to the vaporizing chamber and configured to be coupled to a patient breathing circuit via a pneumatic quick disconnect output; and
a heating element electrically coupled to an electrical connector;
a power source electrically coupled to the heating element via the electrical connector; and
a controller electrically coupled to the power source and storing executable instructions in non-transitory memory that, when executed, cause the controller to:
adjust an amount of power provided by the power source to the heating element based on an anesthetic agent concentration setpoint;
track anesthetic agent usage based on the anesthetic agent concentration setpoint;
determine a remaining anesthetic agent volume in the sump based on the tracked anesthetic agent usage; and
output an alert responsive to the remaining anesthetic agent volume decreasing below a threshold volume.

12. The system of claim 11, wherein the self-contained cartridge further comprises a venturi fluidically coupling the gas inlet passage and the gas outlet passage, and wherein the vaporizing chamber includes a manifold fluidically coupled to a throat region of the venturi.

13. The system of claim 12, wherein the self-contained cartridge further comprises a capillary pump, the capillary pump including a vaporization zone housed within the manifold and a wick extending between the manifold and the sump and at least partially submerged in the anesthetic agent, wherein the heating element is housed within the manifold and in direct contact with the vaporization zone, and wherein the electrical connector includes a terminal positioned external to the manifold and wires that extend from the terminal to the heating element within the manifold, passing through a housing of the manifold.

14. The system of claim 13, wherein the electrical connector is permanently coupled to the heating element via the wires and removably coupled to the power source via the terminal.

15. The system of claim 11, wherein the self-contained cartridge further comprises:
a gas-tight barrier separated from the sump by a shared wall of the housing;
a heat pipe, a first portion of the heat pipe housed within the gas-tight barrier and a second portion of the heat pipe crossing the shared housing and extending into the sump, the second portion of the heat pipe at least partially submerged in the anesthetic agent; and
a ferromagnetic collar housed within the gas-tight barrier and in direct contact with the first portion of the heat pipe.

16. The system of claim 15, wherein the heating element is an inductive heating element positioned around the ferromagnetic collar and housed within the gas-tight barrier, and wherein the electrical connector includes a terminal positioned external to the gas-tight barrier and wires that extend from the terminal to the heating element, passing through the gas-tight barrier.

* * * * *